United States Patent
Kennedy

(10) Patent No.: US 9,816,071 B2
(45) Date of Patent: Nov. 14, 2017

(54) REPLICATION OF UNDIFFERENTIATED CELLS IN A WEIGHTLESS ENVIRONMENT, USES THEREOF AND A FACILITY FOR SUCH REPLICATION AND THE ACCELERATION OF THE EVOLUTION OF PLANTS AND ANIMALS

(75) Inventor: John W. Kennedy, Stevensville, MD (US)

(73) Assignee: ZERO GRAVITY SOLUTIONS, INC., Boca Raton, FL (US)

( * ) Notice: Subject to any disclaimer, the term of this patent is extended or adjusted under 35 U.S.C. 154(b) by 0 days.

(21) Appl. No.: 13/183,004

(22) Filed: Jul. 14, 2011

(65) Prior Publication Data

US 2013/0086702 A1  Apr. 4, 2013

Related U.S. Application Data

(63) Continuation-in-part of application No. 12/473,973, filed on May 28, 2009, now abandoned, which is a continuation-in-part of application No. PCT/US2007/085821, filed on Nov. 28, 2007, and a continuation-in-part of application No. PCT/US2009/034286, filed on Feb. 17, 2009.

(60) Provisional application No. 60/867,582, filed on Nov. 28, 2006, provisional application No. 61/029,053, filed on Feb. 15, 2008.

(51) Int. Cl.
  *C12N 5/04* (2006.01)
  *A01K 67/00* (2006.01)
  *C12N 5/071* (2010.01)
  *A01K 67/027* (2006.01)

(52) U.S. Cl.
  CPC ............ *C12N 5/0602* (2013.01); *A01K 67/00* (2013.01); *A01K 67/0273* (2013.01); *C12N 5/04* (2013.01)

(58) Field of Classification Search
  None
  See application file for complete search history.

(56) References Cited

U.S. PATENT DOCUMENTS 7,163,821 B2  1/2007  Uemura et al.

OTHER PUBLICATIONS

Mashinsky et al. (Cosmic Research, vol. 39, No. 4, (2001), pp. 317-327).*
Thomashow et al. (Annu. Rev. Plant Physiol. Plant Mol. Biol., (1999), pp. 571-599).*
Castellar et al. (J. Plant Biochemistry & Biotechnology vol. 6, 97-100, Jul. 1997).*
Tuszynski et al. "Physical interpretation of microtubule self-organization in gravitational fields" Physics Letters A; vol. 340, Issues—4, 6, pp. 175-180; (Jun. 6, 2005).
Paul et al. "*Arabidopsis* gene expression paterns are altered during spaceflight" Advanced in Space Research; 36, pp. 1175-1181 (2005).

* cited by examiner

*Primary Examiner* — David T Fox
*Assistant Examiner* — Jared Shapiro
(74) *Attorney, Agent, or Firm* — Thompson Hine LLP

(57) ABSTRACT

The present invention provides manufacturing processes for biological replication of undifferentiated plant and animal cells and tissue in a weightless condition, including those systems used in current stem cell research and development and use of undifferentiated parenchyma in plants. The present invention further provides methods for adapting plants and animals to survive outside their native environments. In particular, undifferentiated cells from plants or animals are replicated under weightless conditions in which cell replication or proliferation is accelerated and sustained. Under such conditions, the undifferentiated cells can be "forced" to express sets of genes useful for survival in particular environmental conditions. In this manner, cells surviving prolonged exposure to specific environmental conditions can be selected for and cultivated to produce an organism adapted to that particular environment in an accelerated manner. Methods of identifying specific genes associated with adaptation of a plant or animal to a specific environment are also disclosed.

8 Claims, 3 Drawing Sheets

Figure 1:
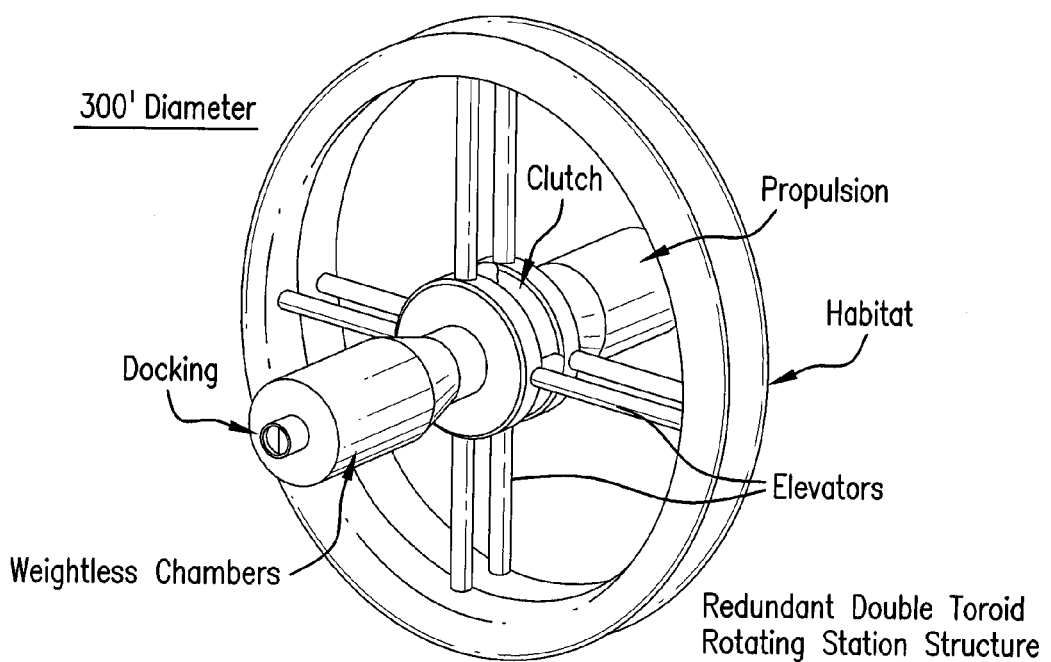

REPLICATION OF UNDIFFERENTIATED CELLS IN A WEIGHTLESS ENVIRONMENT, USES THEREOF AND A FACILITY FOR SUCH REPLICATION AND THE ACCELERATION OF THE EVOLUTION OF PLANTS AND ANIMALS

CROSS REFERENCE TO RELATED APPLICATIONS

This application is a continuation of U.S. patent application Ser. No. 12/473,973, filed May 28, 2009, which is a continuation-in-part of PCT/US2007/085821, filed Nov. 28, 2007, which claims priority to U.S. Provisional Application No. 60/867,582, Nov. 28, 2006, which is herein incorporated by reference in its entirety. U.S. patent application Ser. No. 12/473,973 is also a continuation-in-part of PCT/US2009/034286, filed Feb. 17, 2009, which claims priority to U.S. Provisional Application No. 61/029,053, which was filed on Feb. 15, 2008, which is herein incorporated by reference in its entirety.

BACKGROUND OF THE INVENTION

A weightless condition on space orbit has produced many effects on visitors to that region. Gravity still is present on orbit and through the course of interplanetary travel, but normal plant and animal functions as is known on Earth do not function in the same manner. If gravity acts as a dominant force in a weightless condition, then the reproduction of cells would follow the normal or close to normal pattern experienced on Earth. Evidence indicates that it is weightlessness and not gravity that drives the biology of both plants and animals on space orbit and during interplanetary transits and human travel.

Weight is a physical attribute and force parameter. Weight is a condition wherein the "escape force" [as a function of the angular velocity of a mass (angular momentum)] around a gravitational mass is less than the specific value of the gravitational force. That is, when a body is at rest on the Earth (stationary), it has an angular velocity due to the Earth's rotation. This angular velocity opposes, to some extent, the gravitational force that draws the mass to the center-of-gravity point of Earth. As the angular velocity of the mass increases, the inertial force that opposes the gravitational force increases, to the extent that a sufficient increase will result in the gravitational force equaling the inertial force.

This is the case for masses that have been launched from Earth and are in an orbit of equilibrium around the Earth, i.e. "on orbit". If the Earth had no angular velocity (i.e.—it did not rotate), the weight of a mass would be greater than for a mass on a rotating Earth. It should be noted that the Earth's rotation has only a small effect on "gravity" (actually on "weight"), about 0.5%.

Weight is a condition that results from either (a) the presence of a mass within a gravitational field and/or (b) a mass that is subjected to an external force that accelerates that mass (inertial gravity). Weight, as described in (a) or (b), results from a "mass-acceleration" force so universal and common on Earth that it is normally perceived as an ever-present attribute, state, or condition and is not included in many patent process and protocol parameter descriptions. "Weight" is a normal condition and physical parameter that affects "Living Systems" on Earth. Perceived weightlessness is experienced on orbit or in orbiting spacecraft that have reached a constant velocity on orbit or en-route to interplanetary destinations.

Biological organisms, and specifically most higher-ordered biological organisms, including plants, animals, including humans, hereafter referred to as "High Order Living Biological Systems" (HOLBS) are adapted to Earth's gravity. The effects of weightlessness on plants and animals are expressed by physiological effects that alter the physiology and the morphology of the HOLBS, causing deleterious, irreversible, compromising, and transmuting effects from exposure to such conditions. For example, microgravity has been shown to have an impact on an astronaut's body in space. The effects of gravity in plants and animals and the biological mechanisms involved in adapting to weightlessness may be studied under real microgravity conditions. For example, research on astronauts has shown that body function is disturbed in microgravity. Space agencies are therefore continuing their research in hope of eventually reducing or eliminating some of these undesirable physical effects that appear during a stay in space.

Generally, exposure of living systems to weightlessness results in biological degradation. This degradation is a result of biological processes that have been fundamentally altered due to the absence of an essential force, gravity that is an essential component of those biological processes. Prolonged exposures to a weightless environment correlate to increased biological alterations and degradations. It is the attribute of "weightlessness" or "an apparent absence of gravity induced-force" and/or the "absence of inertially-produced force" that is the critical physical parameter which affects physiological process of living systems in a weightless environment.

On-orbit environments, e.g., as would be found on the International Space Station (ISS), are referred to as zero-g, zero-gravity, and gravity-free environments. These terms are misleading and incorrect. The term "weightless" is more correct and can be equated to "micro-gravity" for our purpose.

The Earth's "gravitational field," whether in LEO, GEO or other orbits (600 km altitudes, etc), is still present, i.e.—90+% of the gravitational field and gravitational force amplitude remains. More precisely—static, on-orbit environments exhibit "weight-free" conditions, wherein gravity forces remain substantial as a consequence of a continuing presence of Earth's gravitation field. For example:

On Earth at Sea Level: Assumption: Gravity=1.00, Weight=1.0.

On Orbit* at 600 km: Then Gravity=0.98, Weight=0.0.

*Static environment: zero local acceleration.

All mass, including the space vehicle and pay load will be at zero weight on a earth bound scale that measures "weight". However, it should be noted that gravity is still present. The force of gravity between a spacecraft and Earth is directly proportional to the product of their masses and indirectly proportional to the square of the distance between them. Acceleration of a mass into orbit overcomes the force of gravity and the mass will enter what is considered to be a "free-fall" effect. The mass in orbit may be a combination of many objects (masses) that appear to be weightless in relation to the other masses in an apparent weightless "free-fall" environment. Gravity forces are still present, but the HOLBS are not able to function properly without a force that mimics gravity.

As noted above, HOLBS exhibit marked physiological and biological changes when resident on-orbit, e.g., given that this environment is where Gravity=0.95-1.00 and Weight=0.00-0.10, it is concluded that it is the attribute of "weightlessness" that links these activities and processes, and that it may appear to be constant without regard to gravity.

More specifically and to further clarify, it may be stated that on Earth, all higher-order living systems, plants, animals, including humans, proceed with biological processes under the influence of a "constant acceleration of their mass." On Earth, this constant acceleration is a result of Earth's gravity, and the endless, largely constant, angular acceleration associated with Earth's gravitational force. It is recognized that there are slight (=<0.5%) variations in gravitational forces and Earth rotation angular velocities that occur depending upon the location and region the mass is on the Earth.

On orbit, in a static environment (no apparent inertial acceleration is present and angular velocity is relatively constant), near-weightlessness (commonly referred to as zero-gravity or micro-gravity) conditions are achieved. These terms are misleading and the terms should be: zero-weight or micro-weight or some equivalents. The term "weightlessness" is being used herein to collectively refer to these conditions. It is therefore evident that it is the attribute of "weightlessness", not gravity, that is critical to active biological processes and components of plants, animals, humans, and higher-order living systems.

Furthermore, it is evident that commonly referred to conditions such as "hyper-gravity," are misnomers, as the term has been associated with the forces resulting from the use of centrifuges that create "artificial gravity", when in actuality, they produce centripetal, angular acceleration forces that are more accurately "inertia produced angular accelerations," and may be viewed as or termed "inertial gravity" or more accurately "hyper-weight". Linear accelerations also apply here: in the form of artificial gravity, especially on long space flights in the acceleration and de-acceleration phases. In summary, an angular (or linearly) induced acceleration of a mass will result in a force upon that mass that causes that mass to possess "weight". Weight is an attribute of acceleration of mass (evidenced elementarily by its unit of measure being in—meters/per second/per second).

Thus, it is submitted that a linkage exists between mass-acceleration (as a mass-energy function) and mass-density (as a mass function), and that the linkage of these two attributes has specific direct and indirect effects upon certain biological processes that occur in plants and animals, including humans and higher-order living systems (HOLBS), where these effects impact functions of cellular replication, reproduction, regeneration, creation, differentiation, specialization, function, cell life-span, suspended animation, and cell death.

It is evident that specific, fundamental biological processes possessed by plants, animals, humans and higher-order organisms and living systems and their growth, development, and life-cycles are affected by weightlessness, and, that these living processes differ critically and profoundly when those processes occur in a "weight" (mass-accelerating) environment versus a "weightless" (mass-zero-accelerating) environment. Therefore it is submitted that it is the attribute or characteristic of "weightlessness" that determines and assures and drives certain essential plant, animal (including humans) and higher-living system processes and not the presence of gravity, nor the presence of a gravitational field or its effects.

Single celled organisms such as bacteria reproduce with little differentiation unless there is a mistake in the normal cells development that may produce a new strain. Bacteria can reproduce at amazing rates. Bacteria are protected by a cell wall that surround the protoplasm. The asexual reproduction of the bacteria continues until regulated by outside forces. Weightless conditions do not appear to be a factor in the reproduction of single celled bacteria over at least one generation.

The replication of undifferentiated cells from both plants and animals may also follow the same model as the yeast if proper preparation, transport and retrieval process are followed for the production of undifferentiated cells on orbit.

Experiments and the data derived from visitors to weightlessness indicate that weightlessness plays a role in the development of human cells. See e.g., Longnecker et al., ed., "Review of NASA's Longitudinal Study of Astronaut Health," Jan. 20, 2004, The Institute of Medicine, which is herein incorporated by reference in its entirety. The Earth's gravitational force influences the developing cells to differentiate into specialized cells, which in plants may be branches or roots and in animals the brain or the legs. In weightlessness, the differentiation of the primordial cells in both plants and animals cannot occur. The continuous reproduction of the primordial tissues will continue with the right nutrient system producing undifferentiated cells in both plants and animals until terminated.

There are techniques that work on a limited basis for both plants and animals in a gravity environmental condition. The constraints are enormous and only a limited amount of primordial cells are available. The use of a manufacturing process that can produce an unlimited supply (based on logistics) of undifferentiated plant and animal cells can be achieved using zero gravity during the replication of undifferentiated tissues. The present invention recognizes the effect of weightlessness on animal and plant cells and utilizes this recognition to provide a method for replicating large quantities of undifferentiated cells for both animals and plants. Additionally, the present invention comprises a space-based on-orbit manufacturing facility for creation, replication, production, storage and ultimate transport of undifferentiated stem cells from a weightlessness environment to a gravity environment on Earth or at another facility. Currently used space vehicles can be used for the replication of stem cells and undifferentiated plant cells.

The plant studies described herein and conducted on the space transportation system (STS)-118 mission demonstrate cell replication rather than cell differentiation and that the cells replicating in space demonstrate a greater mass than the control cells on Earth, thereby demonstrating replication of undifferentiated cell in weightlessness. These results allow a further expansion of the basic logic to include the acceleration of gene expression in undifferentiated cells on orbit and using the protocol discussed herein to provide for a acceleration of the natural selection process for plants and animals.

The accelerated and sustained proliferation of undifferentiated cells on orbit provides an opportunity to "force" the cells to express genes that will enable them to adapt to specific environmental conditions. In other words, imposing environmental constraints on the undifferentiated cells while they are proliferating will result in a subset of cells expressing the necessary genes which enable the cells to survive in that specific environmental condition. One can then cultivate an organism from these selected cells that will survive in that particular environmental condition. For example, undifferentiated cells from a species of citrus plant can be propagated at cooler temperatures on orbit. Cells surviving the cool temperature conditions can be returned to earth and cultivated to produce a citrus plant than can thrive in cold temperature environments.

These techniques are applicable to both plant and animal cells. "Hardy" organisms can be produced by selecting undifferentiated cells expressing genes for survival in particular environments, including extreme environments, such as the surface of Mars. The present invention recognizes the advantages of replicating primordial cells on orbit, and utilizes these advantages to expand the range of cell function thus accelerating the evolution of organisms. Therefore, the present invention provides methods for adapting plants and animals to survive outside their native environments.

SUMMARY OF THE INVENTION

In one aspect, the present invention provides a method of using at least one undifferentiated cell as a result of uniting two haploid cells to form a diploid single cell under conditions to support fertilization in a weightless condition or environment, wherein said the diploid cell can replicate itself continuously to provide a mass of undifferentiated cells.

In one embodiment, the present invention comprises uniting a sperm and egg from an animal or pollen and ovary from a plant to form a single cell in a weightless condition.

In another embodiment, the present invention further comprises uniting two haploid cells, such as a sperm and egg from an animal or pollen and ovary from a plant to form a single cell in a weightless condition or environment, and culturing the single cell to replicate in a weightless condition or environment.

In yet another embodiment, the present invention additionally comprises uniting two haploid cells, such as a sperm and egg from an animal or pollen and ovary from a plant to form a diploid single cell in a gravity condition or environment, such as under normal Earth gravity, after unification or fertilization is complete, immediately preserving cooling to below metabolic activity) the resulting single cell so that no replication of the single cell occurs, then under weightless conditions, reviving the single cell, and culturing the single cell in a weightless condition or environment to obtain replication of the single cell.

In yet another embodiment, the present invention also comprises a diploid single cell, such as a fertilized egg or single cell produced by uniting a sperm and an egg in an animal or pollen and ovary from a plant under conditions to support fertilization in a weightless environment or condition.

In one embodiment, the present invention further comprises one or more undifferentiated diploid cells produced by uniting two haploid cells, such as a sperm and an egg from an animal or pollen and ovary from a plant under conditions to support fertilization resulting in a fertilized egg or diploid single cell in a weightless environment or condition and by culturing the fertilized egg in a weightless environment or condition resulting in the replication of the fertilized egg so that one or more undifferentiated cells are replicated.

In another embodiment, the present invention further comprises the use of already undifferentiated tissues from liver, kidney, etc. of animals (including humans) properly preserved (cooling, etc.) for transport to on orbit for replication.

In yet another embodiment, the present invention encompasses the use of undifferentiated plant tissues for the purpose of replication of the undifferentiated cells on orbit en masse.

In another aspect, the present invention additionally comprises a method of administration of the undifferentiated cells to a subject or patient in need of treatment by the undifferentiated stem cells, wherein the cells are produced by uniting two haploid cells, such as a sperm and an egg from an animal of the same blood type to support replication of the same tissues or from replication of the undifferentiated tissues produced on orbit.

In some embodiments, the present invention additionally comprises known manufacturing, processes, biological processes, cellular, organism, organ, and living-systems development, creation, fabrication, harvesting, growth, replication, reproduction, in-vivo, in-vitro, or equivalent activities, suspended animation processes, development actions, or processes that are undertaken in a weightless environment, or more specifically in a mass-acceleration environment.

In another aspect, the present invention provides structures and processes for on-orbit vehicles, systems, spacecraft, space ships, and related habitats and containments used to transit to and/or travel to distant destinations, wherein those structures and processes resident or part of those structures are configured in a fashion, such that they will lower, reduce, mitigate, or eliminate the biological degradation of plants and animals (including humans) in space, in weightless environments, on-orbit, during interplanetary transits or excursions, and when resident on sub-G environments (Moon, Mars, etc).

In yet another aspect, the present invention provides methods of adapting a plant or animal to grow in a hostile environment or an environment outside of the plant's or animal's native environment. In a preferred embodiment, the method comprises culturing undifferentiated cells from a plant or animal in a weightless condition that mimics at least one element of the hostile or non-native environment to which the plant or animal is to be adapted; selecting the cells that replicate in said condition; and cultivating said selected cells to produce plants or animals, wherein the plants or animals are adapted to grow in said hostile environment.

In one embodiment, the method further comprises evaluating the resultant plants or animals in the hostile environment. The organisms may be evaluated on various criteria including length of survival, growth rate, reproductive capability, cell structure, hardiness in hostile or non-native environments and other gene expressions including but not limited to those enumerated above.

Various environmental stimuli can be used in the methods of the invention to induce the adaptation of the plant or animal to the hostile environment. These stimuli may include excessive heat, excessive cold, low barometric pressure, excessive radiation, high carbon dioxide levels, low humidity, high humidity, drought conditions and duration of sunlight exposure and other environmental factors to mimic conditions in a climate other than the present native climate of the plant or animal.

The present invention also provides methods of identifying genes associated with adaptation of a plant or animal to a hostile environment. In one embodiment, the method comprises culturing undifferentiated cells from the plant or animal in a weightless condition that mimics at least one element of the hostile environment to which the plant or animal is to be adapted; selecting the cells that replicate or proliferate in said condition; examining the gene expression profile of the selected cells in comparison to the gene expression profile of control cells; and identifying genes that have a change in expression level, wherein the identified genes are associated with adaptation to the hostile environment. The selected genes that are differentially expressed in the various environmental conditions can be further used to produce transgenic plants and animals with the desired adaptive characteristics by introducing these genes into cells that mature into plants or animals. Through this process, the adaptation and/or evolution of plants and animals can be accelerated.

In another embodiment, the method can be used for the production of vaccines to be used in animals and humans. By stressing pathogenic microorganisms on orbit, modified strains of microorganisms can be produced. These can include less virulent and/or more virulent strains of bacteria and viruses, which can then be utilized for the production of improved vaccines.

BRIEF DESCRIPTION OF THE FIGURES

FIG. 1. A 3-dimensional on-orbit manufacturing facility useful for manufacturing stem cells and stem cell tissues in a weightless environment.

FIG. 2. A robotic processing system for on-orbit manufacturing of plant and animal undifferentiated cells useful in the present invention.

FIG. 3. Gene expression profiles of *Arabidopsis thaliana* seedlings on orbit and on Earth. The gene expression pattern from orbit is plotted versus the gene expression pattern on Earth (panel A). Panel B depicts a subset of the gene expression profile to illustrate heat-shock and CAB (light) genes. The lines labeled with 4× and 10× illustrate four-fold and ten-fold threshold levels of expression, respectively.

DETAILED DESCRIPTION OF THE INVENTION

The present invention provides manufacturing processes for biological reproduction of plants and animals in a weightless condition, including those systems used in current stem cell research and development and use of undifferentiated parenchyma in plants.

In one embodiment, the present invention provides a method of replicating at least one undifferentiated cell comprising uniting two haploid cells to form a diploid single cell under conditions to support fertilization in a weightless condition or environment, wherein said diploid single cell can replicate itself forming another diploid cell and wherein said diploid single cells will not develop into an embryo of differentiated cells and tissue. The two haploid cells may be gametes, and more specifically the gametes are of the opposite sex or mating types.

The present invention includes the use of the purest form of undifferentiated tissues of organs such as, but not limited to liver and kidneys that are replicated on orbit. The present invention comprises uniting a sperm and egg from an animal or pollen and ovule from the ovary from a plant to form a single diploid cell, such as zygote, in a weightless condition or environment as defined herein. The single cell will not divide to ultimately produce differentiated cells with the capability of developing into an embryo when created or produced or cultured under a weightless environment. Then the replication of cells from newly united sperm and egg or pollen and ovary in a weightless condition provides an endless supply of undifferentiated cells and tissues that can be used to reproduce cells that are identical to the parent cells without transformation into multi-celled, differentiated tissues. One or both of the haploid cells utilized in the method may contain an incomplete haploid genome of the cell, and could be missing genetic material or genes or fragments thereof.

The present invention further comprises uniting two haploid cells, such as a sperm and egg from an animal or pollen and ovary from a plant to form a single diploid cell in a weightless condition or environment, and culturing the single cell to replicate into undifferentiated or primordial cell and tissue in a weightless condition or environment. The method further comprises culturing the diploid single cell to obtain multiple replications of the replicated single cells to a suspension of undifferentiated cells. The method further comprises harvesting the undifferentiated cells from the suspension. Additionally, the method further comprises changing the culture conditions of the suspension or harvested undifferentiated cells to a state of suspended animation or quiescence.

The present invention further intends to encompass a method of producing or replicating at least one undifferentiated cell comprising uniting two haploid cells to form another diploid single cell under conditions to support fertilization in a gravity condition or environment under normal earth gravity, after unification is complete, preserving the resulting diploid single cell so that no replication of the diploid single cell occurs, reviving the diploid single cell under a weightless condition or environment, and culturing the diploid single cell in culture medium in a weightless condition or environment to obtain replication of the diploid single cell that will not develop into an embryo of differentiated or primordial cells and tissue. The two haploid cells may be gametes, and more specifically the gametes are of the opposite sex or mating types. Further, the gametes are a sperm and an egg from an animal or a pollen and an ovule from an plant. The diploid single cell can be a zygote. Additionally, at least one of the haploid cells comprises an incomplete haploid genome of said cell.

The method further comprises culturing the diploid single cell to replicate in a weightless condition or environment. Further, the method further comprises culturing the diploid single cell to obtain multiple replications of the replicated singles cells to a suspension of undifferentiated cells. The method further comprises harvesting the undifferentiated cells from the suspension, and optionally, changing the culture conditions of the harvested undifferentiated cells to a state of suspended animation or quiescence. Or alternatively, the method further comprises changing the culture conditions of the suspension of undifferentiated cells to a state of suspended animation or quiescence. Also encompassed by this method, is an isolated diploid single cell produced by the methods described herein. This single cell can be a zygote. Additionally, a composition comprising more than one single cell produced by the methods described herein is disclosed that is optionally mixed with a pharmaceutically acceptable carrier.

The present invention further comprises uniting two haploid cells, such as a sperm and egg from an animal or pollen and ovule from the ovary of a plant to form a single diploid cell in a weightless condition or environment, and culturing the single cell to replicate into undifferentiated or primordial cell and tissue in a weightless condition or environment.

The method further comprises culturing the diploid single cell to obtain multiple replications of the replicated single cells to a suspension of undifferentiated cells. The method further comprises harvesting the undifferentiated cells from the suspension. Additionally, the method further comprises changing the culture conditions of the suspension or harvested undifferentiated cells to a state of suspended animation or quiescence.

The present invention also comprises a fertilized egg or single cell produced by uniting a sperm and an egg in an animal or pollen and ovary from a plant under conditions to support fertilization in a weightless environment or condition. An isolated diploid single cell produced by the method described herein, and wherein the diploid single cell comprises a zygote which can be replicated without development into further stages.

The present invention further comprises a method producing at least one undifferentiated cell comprising uniting a sperm and egg of an animal prior to culturing in a weightless condition or environment to produce undifferentiated cells that replicate at a higher rate than in a weight or gravity condition or environment.

Also encompassed by the present invention is a composition comprising more than one single cells (diploid) of produced by the method described herein, and optionally a pharmaceutically acceptable carrier. Such a diploid single cell comprises a zygote that will not progress into a further stage of development unless prompted to do so.

The present invention further comprises one or more undifferentiated cells produced by uniting a sperm and an egg from an animal or pollen and ovary from a plant under conditions to support fertilization resulting in a fertilized egg or single cell in a weightless environment or condition and by culturing the fertilized egg in a weightless environment or condition resulting in the replication of the fertilized egg so that one or more undifferentiated cells are produced or replicated.

The present invention additionally comprises a method of administration of an effective amount of the undifferentiated cells produced by the methods of the present invention to a subject or patient in need of treatment by the undifferentiated cells, wherein the cells are produced by uniting two haploid cells, such a sperm and an egg from an animal or pollen and ovary from a plant under conditions to support fertilization to for a fertilized egg or single cell in a weightless environment or condition and by culturing the fertilized egg in a weightless environment or condition resulting in the replication of the fertilized egg so that one or more undifferentiated cells are produced or replicated. The subjects treated may be in need of undifferentiated cells to treat diseases and conditions, such a type I diabetes, Parkinson's disease, Alzheimer's disease, blood diseases, such as leukemia, different types of anemia, systemic lupus, autoimmune diseases and deficiencies, heart tissue repair, bone and cartilage repair, eye and skin repair to name a few of the conditions and diseases that can benefit from the undifferentiated stem cells produced by the present invention. The stem cells will be administered utilizing known methods presently used for the administration of adult stem cells to patients. Known pharmaceutically acceptable carriers can be mixed with the composition comprising the undifferentiated stem cells produced by the methods of the present invention under weightlessness conditions or environments to form a pharmaceutical compositions comprising the undifferentiated stem cells and optionally a pharmaceutically acceptable carrier.

The present invention additionally comprises manufacturing processes, biological processes, cellular, organism, organ, and living-systems development, creation, fabrication, harvesting, growth, replication, reproduction, in vivo, in vitro, or equivalent activities, suspended animation processes, development actions, or processes that are undertaken in a weightless environment, or more specifically in a mass-acceleration environment wherein the mass-velocity is near-constant and the mass-acceleration is near-constant and is of a value which is equal and opposite to the force-value of gravity present.

The present invention further comprises processes, manufacturing, development, prototyping, activities and actions that are directed to the development, replication, reproduction, growth, maturation, or creation of new cellular materials, tissues, cellular components, organs, living systems, and suspended animation technologies—specifically when those activities are in a near weightless or fully weightless condition.

The present invention also comprises a culture device for replicating a diploid cell produced by the methods disclosed herein and a method for manufacturing, processing, storing (including suspended animation) and shipping cells created by the unification of animal (sperm and egg) and plant (pollen and ovary) for the purpose of replication of primordial also known as undifferentiated cells and tissues, including, but not limited to animal, such as human, stem cells and plants (undifferentiated tissues such as apical meristems), and other tissues, specifically being methodologies that utilize processing environments, wherein, the forces of weigh are absent, specifically near-weightless and fully-weightless environments and processing conditions.

The present invention additionally comprises those structures and processes for on-orbit vehicles, systems, spacecraft, space ships, and related habitats and containments used to transit to and/or travel to distant destinations, wherein those structures and processes resident or part of those structures are configured in a fashion, such that they will lower, reduce, mitigate, or eliminate the biological degradation of plants and animals (including humans) in space, in weightless environments, on-orbit, during interplanetary transits or excursions, and when resident on sub-G environments (Moon, Mars, etc).

All of the manufacturing processes, biological process, and related actions and activities conducted on Earth, are subject to and include a "mass-acceleration" component. A forcing component that results in a condition or characteristic known as "weightlessness" is encompassed by the present invention.

Gravity is not the direct force or condition that drives biological processes in a weightless environment. Gravity on Earth, for example, is the condition that results in forces that drive the biological universe on Earth. Gravity is not absent on-orbit. Substantial gravitational fields exist on-orbit and in space. The gravity on orbit is approximately 95% the gravity on Earth and approximately 0% weight. The rules regarding reproduction of cells change in a weightless condition. Both plant and animal cells do not replicate in a weightless condition according to the rules on Earth. On Earth, gravity is a condition that ties to specific forces that govern the reproduction of cells.

Gravity is a condition which may contribute to "weightlessness" or "weight" depending upon the presence of other forces, i.e.—other conditions, energies, or forces which result in the acceleration of mass present, and which may add to or oppose the effects of mass-acceleration that result from the presence of mass within a gravitational field. In a weightless condition (where the acceleration of mass is generally equal to and opposite the force that exists from gravitational conditions), gravity is a null-component of the system and does not have a unique, essential, critical, or driving effect upon the biological processes described and claimed herein.

To clarify the present invention with respect to gravity, gravity forces and gravitational fields, it is recognized that gravitational fields and forces exist to varying degrees and at varying amplitudes on Earth, in the Earth, at altitudes above the Earth, on-orbit around the Earth, between Earth and Moon, and inter-planetary in the Solar System and beyond. The gravitational field forces in these regions vary from approximately 1 G on Earth, to 0.4 G, to 0.6 G on Mars, etc., and at other varying amplitudes throughout the Solar System. It is recognized that these gravitational force scalars (values) remain, whether or not other inertial forces are present. It is recognized that gravitational forces at any particular point within the Solar System, vary temporally given the motions of the planets and heavenly bodies present within the System. It is recognized that gravitational forces present on local systems, e.g.—Earth, Moon, Mars, are relatively constant and that local gravitational field amplitudes in these point regions are relatively constant in amplitude over time.

The present invention recognizes that an essential and critical constellation of processes associated with the reproduction of cells is uniquely and profoundly different in a weightless condition, than where those processes are conducted or performed or executed in an environment where (a) gravity that results in mass-acceleration exists, (b) on Earth, (c) in artificial gravity environments [i.e.—inertial gravity environments e.g.—centrifuges, so-called hyper-gravity, more correctly termed hyper-weight) systems, units, devices, or facilities.] The nature of all reproduction processes are influenced by gravity and cells continue to replicate under the influence of the gravitational force, following a genetic code prescribed in the genes that respond to the force of gravity. A fertilized egg replicates, and begins forming unions and congregate into a mass that expands exponential fashion (1, 2, 4, 8, etc.) to eventually form an embryo, then differentiated cells and tissue. The present invention is different from the development of the cells in the gravity environment, in that the weightless conditions result in the replication of cells to form cultures of undifferentiated cells that do not develop into an embryo. In weightless conditions, a fertilized egg can be replicated indefinitely to form cultures of undifferentiated cells that do not develop into an embryo.

Methods of preparing such undifferentiated cell cultures in weightless environments and their use are described herein. Plant experiments on the STS-118 mission demonstrated that plants replicate in weightlessness and since both plants and animals follow the Kreb's Cycle, animal cells similarly replicate in weightlessness.

The present invention further comprises the biological and living-system processes, manufacturing, cellular, replication, reproduction, creation, duplication, harvesting, development, maturation, and growth, processing storage (including suspended animation and shipping) that are conducted or performed, whether through human or autonomous-control, in (process) environments that have zero-acceleration of mass in orbit or in interplanetary travel and/or where the acceleration of mass is equal and opposite the gravity induced force present.

To further clarify those process environments where there is no mass-acceleration force present and/or where the acceleration of mass is equal and opposite the gravity induced force present, no mass-acceleration force is included as part of the biological, physiological, replication, reproduction, growth, harvesting, manufacturing, or production operation on orbit or in interplanetary travel unless artificially produced.

The present invention further comprises all "replication" processes where plants and/or animals including humans, and higher-order organisms and living systems "HOLBS" and the cellular processes of which they are based-upon duplicate their cellular constituents, most specifically and critically, those cellular aspects and types which are primordial in structure and biological configuration.

The present invention comprises the "replication processes" as contrasted to normally occurring "reproductive processes" in orbit or during interplanetary travel. Wherein those cellular activities that progress through normal maturation stages and cycles are known as "reproductive" on Earth, however, on orbit, cellular activities that "duplicate" and "replicate" copies of cells that are identical in structure and function to their originating predecessors is "replication" and the process, storage (including suspended animation) and shipping is encompassed by the present invention.

Wherein, specifically, the creation of, processing, and manufacturing of "primordial stem cells" from animals, undifferentiated parenchyma from plants and from other primordial tissues are central to the present invention, and where these processes are defined and termed as being "replication", not reproductive.

The present invention further comprises processes that occur or are performed in zero-acceleration of mass environments and/or where the acceleration of mass is equal and opposite the gravity induced force present. In one embodiment, the present invention comprises processes where the production of "undifferentiated tissues, stem cells—of any stage or type or maturation, of primordial cells, of zygotes, sperm, egg, pollen, are part of said processes, and particularly wherein the objective is the manufacture, creation, growth, development, harvesting or production of these cellular masses, tissues, organisms, and/or similar living systems.

The present invention comprises processes that enable the "replication" of a single cell from newly united sperm and egg or pollen and ovary in a weightless condition that under continued weightless conditions will provide an endless supply of undifferentiated cells or tissues that can be used to reproduce cells that are identical to the parent cells without transformation into multi-celled tissues or differentiated tissues.

In animals and plants, the sexual stage of the organism is one celled for the male (sperm or pollen) or female (egg or ovary). Both the sexual stage of plants and animals are also protected by cell walls. Such cells can be transported into orbit without interference for use in the replication phase of undifferentiated cells. The selection of the cells being used for replication must be conducted with great care to ensure the germ plasma will be a match with the use intended. For example, matching blood types from a donor cell with the blood types of an eventual recipient is a criteria. The plant and animal single-celled male and female sexual stages are also single celled and are not effected by gravity in limited experimentation. Formation of a zygote occurs after the union of the egg and sperm and exists up until the point that the cell replication begins. It is at this stage that the cells in either plants or animals can differentiate into any part of the plant or animal.

Furthermore, the present invention comprises all manufacturing processes for biological replication and reproduction of undifferentiated cells of both plants and animals in a weightless condition.

The present invention also comprises all processes and systems used in current stem cell research, development, processing, and manufacture, but with the additional step or condition of performing or conducting these processes in a "weightless" (zero-acceleration of mass) environment as defined in the present invention and as understood by persons skilled in the art of gravitational theories and sciences, and/or where the acceleration of mass is equal and opposite the gravity induced force present.

By way of further clarification, the above-described invention comprises all stem cell, cellular, tissue, biological entity, and living organism processes and processing and all processes and process patents for same, applied for, pending, filed, and issued that predicate their disclosed inventions on processes that are conducted either (a) on Earth or (b) in an environment wherein there is an energy, force, or equivalent process that includes a significant "mass-accelerating" component or free-fall effect as previously described. However, the present invention distinguishes its embodiments from these known processes by performing all of the steps and processes including cultivation of or culturing the resulting replicated cells in a weightless environment. In other words, the disclosed or known process elements, contents and activities are conducted in an environment where the constituents (cells, tissues, organs, organisms) have weight (and where the origins or causes of that weight may be from either gravitational or inertial energy sources), such as performed on Earth in its gravitational environment.

In a further embodiment, the present invention comprises the use of undifferentiated parenchyma in plants and undifferentiated stem cells in animals as a unique process component for plant and animal replication for mitigation of diseases or arthropods.

Biological systems concerning the replication of cells adjacent to reproductive tissues in mature animals or plants in a weightless condition do not follow the rules for a gravity condition, but rather follow a non-descript process that provides for replication of primordial tissues without differentiating into a conglomeration of cells to form a plant or animal. Space visitors have reproduction of cells that mimic but do not follow the normal reproduction into a functional cell. The primordial cells adjacent to bone, muscle, nerve and other types of differentiated cells and the mass of cells that produces blood and hormones, do not function as in a gravity or other force field (accelerated mass), and form non-functional cells. Space visitors experience this effect and indicate that cell reproduction is not normal. It is believed that the cells being reproduced are undifferentiated with minimal influence from the adjoining tissues with a result being non-functional tissue.

The primary cell to be used for stem cell replication is formed by the union of a sperm and egg in animals and can be conducted in a weightless (in orbit) environment. In plants, the apical meristem cells (undifferentiated parenchyma) resulting from the union of pollen and an ovary in a weightless condition can provide an unlimited supply of identical cells that do not differentiate at the time of replication. The present invention is intended to encompass all processes currently used and known by persons skilled in the art for the reproduction of plants and animals in a gravity driven environment for use to replicate cells at the telophase stage of mitosis in a weightless condition.

The present invention is based on the premise that the biological systems including plants, animals, humans, and high-order living systems function in accordance with a newly coined term "K-Law," which states that primordial cells and living tissues will "replicate," which is defined as producing an exact copy in a "zero-acceleration of mass" environment. The "K-Law" states that primordial cells formed in weightlessness will self replicate, but will not proceed to the next step of cellular and tissue replication resulting in cellular differentiation into recognizable plants or animals, i.e.—progressive maturation and differentiation along a recognizable life-cycle path. Stem cell staging, for example, will progress from primordial tissues to adult stem cells, but will not combine with other stem cells to form a zygote.

With regard to the present invention, the "K-Law" is that which is defined by the conditions wherein primordial cells, in a zero-acceleration of mass environment are allowed to develop and that said development is not reproductive, but rather these cells only replicate. The "K-Law" applies and is effective only in "zero-acceleration of mass" environments, or where there is a "net-zero-acceleration of mass" and/or where the acceleration of mass is equal and opposite the gravity induced force present. The present invention further encompasses all processes wherein the "K-Law" applies.

Furthermore, the present invention comprises those processes wherein the primary cell formed by the union of a sperm and egg (in animals, including man) that are processed, produced or created in a weightless environment, including manufacturing, handling, storage (including suspended animation) and shipping of the final product. And wherein, the process for plants is that which employs the apical meristem cells (undifferentiated parenchyma) resulting from union of pollen and an ovary in a weightless condition, such that the result is an unlimited supply of identical cells that do not differentiate at the time of replication into specialized cells and tissue.

The present invention also comprises all processes currently used and known for the reproduction of plants and animals in a gravity driven environment for use to replicate cells at the telophase stage of mitosis in a weightless condition, storage (including suspended animation), handling and shipping of the final product. Further, primordial cells created or produced as a result of the unification of an egg and sperm that have or have not been compromised by another force (example, Earth's gravity) will reproduce identical cells (given mistakes in genetic code) in a weightless environment. Additionally, primordial cells resulting from apical meristem tissue or from the germination of a seed and/or new tissues from another source (new supplies) will reproduce the same undifferentiated cells during mitosis in a weightless environment. The present invention encompasses all known processes that are Earth bound to reproduce cells at the telophase stage of mitosis for the purposes of stem cell replication and/or other purposes but for use in a weightless environment.

The present invention further comprises all Earth bound processes for the replication and manufacturing of undifferentiated tissues from plants and/or animals or both for use in a weightless and/or reduced "gravity" condition. Such conditions include the replication of undifferentiated tissues on the Moon, Mars, etc., or other reduced gravity conditions.

Additionally, the present invention also comprises an orbiting craft, for example, Space Station, to provide a weightless condition. Gravitational forces are still present on such a craft. However, the biological process is not chained to gravity; but the condition of weightlessness. The extensive literature describes the maladies suffered by space visitor, especially in prolonged stays. The present invention provides a unique method of transfer of plants and animals from a weightless condition to a device that mimics the force of gravity on Earth and back again to weightlessness. This method of producing a condition that mimics gravity in an orbiting vehicle will allow animals and plants to survive long periods of space flight.

Long-term visitors to weightlessness are afflicted by many deficiencies during the stay in this environment, especially "wasting" of tissues on a Bell Curve—the longer the stay, the more "wasting" of the body and functions. Exercise machines, etc. have been incorporated into procedures to "condition" visitors to the weightless environment. All have failed to a lesser or greater degree. A "Wheel" circulating around a central unit was impractical because the whole system would rotate. However, the present invention provides a "Clutch" system in which the hub of the system will be at a weightless condition, a secondary "Clutch" that can be stopped at the hub (weightless condition), allowing personnel and/or equipment to be off-loaded and then gain speed to the circulating "Wheel" at intervals to allow for proper balance. The present invention comprises such a vehicle comprising the above described "Wheel" and "Clutch" that will allow for weightlessness experimentation and/or allow for long periods of orbital and/or space travel to distance objective (Mars, etc). The "clutch" and wheel can be composed of composite section that can be transported to orbit and assembled. The "clutch" and wheel can also be constructed of puncture-proof inflatable composites that can be transported to orbit and inflated in two sections for the "clutch" and the wheel. (attachment). The number of "spokes" in the wheel can vary, but weight distribution and balance must be of concern.

The present invention is also intended to encompass a system to be used to develop artificial gravity while still maintaining a weightless condition for the reproduction of undifferentiated tissues of both plants and animals.

The present invention further comprises the system as described can be "mated" with the current space station that can act as a haven for the crew of the Space Station. A universal "mating" system to allow transfer of supplies, personnel and experiments will be incorporated. The space tourism possibilities could also utilize the use of the "clutch" and wheel concept, especially if the space visitor will be in orbit for some time.

By way of further explanation of the present invention, replication of cells in a weightless environment will not reproduce in a normal fashion because a gravitational force must be present to align the components of the primordial cells. For example, germinating seeds on Earth align the roots to go down and the stem to go upward due to the force of gravity. Newly united sperm and egg form zygotes. The present invention is premised upon the theory that cells that are not influenced by a force that is required to properly align the components of a reproductive system will not act according to known understanding of common cell replication. Cells that replicate according to the laws that govern replication will be replaced by a new set of rules (K Law) based on a "weightless" condition that allows a primordial cell to reproduce itself over and over again.

Space visitors have suffered numerous maladies in direct proportion to the time spent in orbit. The visitors are experiencing the result of primordial cell replication adjacent to existing cells where the "new" cells are dysfunctional because there is no force, such as gravity or an artificial gravity-like force, to provide alignment according to the "gravity" instruction. Cells adjacent to muscles, bone, etc. will attempt to reproduce the same cells, but instead produce a cell the looks like the original cell, but does not function properly because the gravity like force was not there to align the components of the cell in proper fashion (K Law). The cells that replicate in space visitors are primordial in nature, and cannot provide tissues adjacent to the tissue (bone, muscle, nerve, blood cells etc) which resemble the same tissues in a Earth environment. Instead the cells produced in a weightless environment will follow the instructions of the adjacent cell, but not reproduce totally viable cells that function as the cells would if on Earth. The references sited attest to the maladies that our space visitors have encountered and are consistent with the (K Law).

Primordial or Undifferentiated Replication in Weightlessness

However, the bad news can be the good news, and knowing the problem will allow a solution. As described herein, in a weightless condition, both plants and animals, cells can replicate to the telophase stage of mitosis and remain undifferentiated. Therefore, a weightless condition allows the production of undifferentiated cells that can be harvested en masse. Without the influence of a gravitational force, it is submitted that cells do not replicate properly beyond the telophase stage of mitosis to form a plant or animal. Cells at the telophase or final stage of mitosis in a weightless condition only replicate the original cell at the telophase stage. Cells produced to the telophase stage of mitosis can be harvested on a continuous basis and immediately stored in a state of suspended animation for transport back to Earth or an out-post where a suitable condition exists for reproduction.

Space Visitors

In a weightless environment, formation of cells adjacent to tissues in a space visitor (red blood cells, bone, muscle, etc.) will form the same cell adjacent to the parent cell, but will be dysfunctional. A different system, but an analogy, is a cell or cells in the body that become a different, but similar cell, because of lack of sufficient oxygen and because of not being oxygenated properly, the cells become anaerobic. Those cells follow a fermentation process and do not follow the "Krebs" cycle, and although the cells will form, they will not be functional. There is a high probability that those cells can become cancerous.

Cells adjacent to normally reproducing tissues (skin, bone, etc) in a space visitor in a weightless condition produce undifferentiated cells that would produce normal cells by instructions by the adjacent tissue and gravity. However, a weightless environment will produce cells that have all the genetic make-up of the adjacent cells (muscle, skin, etc.), but will not be functional.

The basic problem with the reproduction of the primordial cells for commercial purposes of both plant and animals has been a system that compensates for replication of the multi-celled higher plants and animals, but will not replicate cells that reach only mitosis (union of the egg and sperm to formation of a reproductive cell) regardless of the process used. Production of the primordial or undifferentiated cells in both plants and animals in a weightless environment can produce the same tissues during mitosis present in the original union of egg and sperm in animals or plants, and possibly the extraction of apical meristem resulting in the germination of a seed in zero gravity and use of the undifferentiated parenchyma cells.

Current procedures cannot reproduce progeny of the originally united single cell at mitosis. There is a need to develop a process of manufacturing of the primordial cells also known as undifferentiated cells into a source of germ plasma for plants or stem cells for animals (including man). The force of gravity has prevented the establishment of a process that would allow the primordial tissue for replication of both plants and animals in a more efficient and productive manner. Currently the only source of cells at the telophase stage of mitosis is the harvesting of fetus and associated tissues, including the cord tissue and blood from miscarriages obtained from hospitals, clinics and other facilities.

A proposed method is presented herein for reproduction of the cells in mitosis in both multi-celled plants and animals in a weightless environment. The methods used for the reproduction of the cells at the telophase stage of mitosis will be adjusted as necessary by persons skilled in the art, but taken from current technology with modifications to adjust for a weightless condition or reduced gravity, including possible simplification of the process. Gravitational forces may govern the reproduction of animals in a weightless condition, but this fact has provided the opportunity for the replication of cells during mitosis is weightlessness.

The scientific literature describes the differences in the success in the reproductive rate, and more specifically, the longevity of individuals that live at sea level vs. the tallest mountains (note: the criteria is longevity, not mortality). The data only suggests that gravity may be a factor in the reproduction of the human species. A greater success rate for reproduction of the human species is indicated by a greater gravitational force. An overlay of the greatest population centers coincides with those regions with the highest gravity. Gravity on Mars may present a problem for reproduction of the human species as well since the humanoid is not adapted to the reduced gravitational force.

The understanding of cell reproduction in zero gravity provides a further benefit beyond the union of "egg and sperm" in animals and the union of pollen (or equivalent) with a plant ovary. The final stage or telophase of mitosis occurs and replication of the undifferentiated cells results in a population explosion of cells that can be processed and stored in suspended animation, such as freezing in liquid nitrogen or other low temperature environments or other techniques, to ensure suspension of replication, for shipment to a gravitational force for use as totally undifferentiated stem cells in animals and undifferentiated parenchyma (or like tissues) in plants.

The literature supports the premise that compromised" tissues exposed to gravity at conception (produced as a result of gravity at conception) for plants and animals will not reproduce the parent tissue faithfully and indicates serious concerns for space travel for long periods of time. The literature and observations of long-term visitors to zero gravity provide such evidence.

The present invention is premised upon the theory that mitosis occurs in cells from dedicated tissues (bone, muscle, etc.) that does not produce the cells of origin (bone, muscle, etc) but will follow reproduction into cells of origin that may be influenced by, but not in control of the parent cell (bone, muscle, etc). Such cells are not the replication of the parent tissue, nor new undifferentiated tissues, but a "K" cell (new terminology) that has no purpose, but can function. Such factors must be included to incorporate an artificial gravity technology that must be required for any long-term space travel or colonization of the Moon, Mars or any other body with a gravity force of less than one "G".

Methods

Current practices on Earth for unification of egg and sperm in higher order living biological systems (HOLBS) are commonly practiced in the reproduction of man and other animals. These same procedures are useful for impregnation of an egg with a sperm in a weightlessness environment according to the present invention. All procedures used on Earth for impregnation of egg and sperm in HOLBS, and other animals are useful for the production of undifferentiated cells for the production of tissues or for other purposes, such as reproduction of endangered species.

The procedures include, but are not limited to the use of a preserved egg and sperm held in a suspended animation phase that are revitalized using current techniques in a weightlessness environment and allowed to unite to form a single cell. The current techniques and advanced robotic processing are used to unify the sperm and egg to produce a cell capable of replication in the weightless environment described herein. The united egg and sperm preserved immediately upon the unification, can replicate itself without forming a zygote that will develop into an embryo of differentiated cells and tissue, and can be utilized for the purposes discussed (tissue reproduction, reproduction, etc.). The use of the procedure of using preserved egg and sperm of HOLBS and lower order animals in a weightlessness environment when and eggs and sperm are transported to an on orbit facility, processed and unified in weightlessness, allowed to reproduce in a contained space, processed through a transitional production phase that may include, but is not limited to and not necessarily in this order of the coating of the individual cells, to prevent "grouping" (if necessary), gradual cool-down to suspended animation, chemical treatment (if necessary), into a vessel where the replicated cells can be stored in suspended animation. The replicated cells can then be transported back to Earth for uses described.

Additionally, the replication and production as described herein for the unification of pollen (sperm) and ovary (egg) of the equivalency of HOLBS and lower plant life in a state of weightlessness condition for the purpose of production of undifferentiated cells is described herein. The procedure includes, but is not limited to routine isolation of the pyramid cells (undifferentiated tissues) in the apical meristem and culturing the tissues. However, the weightlessness environment will provide an exponential growth of the undifferentiated tissues, yielding high quantities of the cells that may be processed using a coating to preserve hydration and other life-sustaining parameters, a suspended animation process and packaging for transport back to Earth.

The principle is the same whether the cells being replicated for production are animal or plant cells. The cells being replicated are the result of the male and female cell union from animals or plants. This union can be accomplished in weightlessness with great success using the current state of the art used on Earth. Alternatively, the union can be achieved by uniting a female and male cell on Earth under gravity conditions, placing the single cell in suspended animation prior to any cell division of the single formed cell, and transporting the stored cell to orbit or a similar environment for replicated production in weightless conditions.

The single cells produced by union of the female and male (egg and sperm from animals; pollen and ovary from plants) can be replicated as single cells in a production mode that will yield cells at an exponential rate, providing cells for use in tissues for body parts or branches or roots, depending on the progeny.

Plants

The present methods of reproduction of plants include cloning and seeds. Reproduction and use of apical cell reproduction has greatly increased the numbers of plants in a vegetative reproduction process. The process depends on the isolation of the reproducing cells at the tip of a plant or plant part (root, branch, etc) known as the meristem and successful cloning of the limited number of cells at the undifferentiated stage of development at the tip of the plant or other actively growing portions of the plant (root, cambium, etc.). The process is efficient for herbaceous plants, but the "woody" plants cannot be reproduced in high numbers because of the limited availability of apical cells. Cells in mitosis in quantity would speed the introduction of new varieties and species, including endangered species. The commercial advantage would be saving years of time between discovery and introduction of the plant to the market.

The production of an unlimited number of the undifferentiated cells has not been possible because gravitation forces "pull" cell matter into "layers" (starch, etc.) that will start the processing of the undifferentiated cell into specific (differentiated) cells. The process in the presence of gravity allows the cells to differentiate into a stem or a root and guide the plant using gravity to form the stems, leaves, flowers, etc that have been programmed over billions of years to form such structures given the "keys" that that are needed by the genes in the genetic code. However, the plant will perform "naturally" at only one "G" or more to another limit.

Forces exerted by artificial gravity induced have been demonstrated by a few zero gravity experiments where plants were subjected to a "spinning" in the experiment to produce an artificial gravity. The experiment demonstrated that such means of plant production cannot be produced using limited experimentation. The plants were deformed, due to the migration of molecules within the cells (starches). The plant was conditioned to formation of the root vs. stem, etc. in a one "G" situation, the only sequence the plant was acclimated to over a few million years. The plants were also subject to the effects of gravity prior to being sent to zero gravity, and the effect of the "G" factor on the plants may have also contributed to the failure of the experiment. Otherwise designed with the germination of the seeds in a spinning device that would mimic one "G" may have produced a different result, and healthy plants may be produced using this technique.

The plants sent into zero gravity had already been compromised as a result of the initial introduction to gravity after germination and the additional force of the "G" forces from take-off of the mission and had already programmed genetically the plant to produce roots in one direction and stems in another. But it is possible to replicate and produce undifferentiated parenchyma resulting in the unification of pollen (sperm) and egg (ovary) in plants that are unified on Earth, preserved prior to any division of the united single cell, and transported immediately to orbit for the purpose of producing undifferentiated cells capable of replicating identical cells for production of tissues used for parts of plants, and the plant itself, including, but not limited to stems, roots, flowers, seeds, fruits, and other tissues. Such tissues are preserved in a suspended animation state from orbit to use in the field using the current technologies now present on Earth.

The present invention is premised upon the theory that a union of pollen and ovary (egg) in zero gravity will produce a cell that will go to mitosis and then reproduce that cell continually en masse or until a genetic break down in the cell(s) may occur that would disrupt the exponential reproduction of the same mitosis. The newly formed cells can be harvested through an exudation process and stored (including suspended animation) until the cells are shipped back to Earth or some other base camp with sufficient gravity. The cells can then be incorporated using current techniques for use of undifferentiated tissues. The apical cells of plants produced in orbit that reproduce cells in mitosis that will faithfully reproduce the identical cells can be used for multiple purposes.

The current practice for the production of plants by uniting the pollen and ovary on Earth is time-consuming and difficult, but using the undifferentiated growing cells produced in a weightless environment can produce the same results with exponential numbers in comparison. New growth from plant cells and tissue in weightlessness can provide a source of the undifferentiated cells for the manufacture of such cells in an exponential fashion using the techniques described and/or other technologies that exist or to be discovered.

Once produced in a zero gravity environment, the undifferentiated cells at mitosis can be stored and conditioned for a storage, and preparations for distribution of the manufactured cells organized for transportation to gravity and utilized as stock for plants. Undifferentiated plant tissue en masse could be used in the production of fruit tree scions on stock already established. For example, the insertion of the undifferentiated cells from several varieties for a compatible nature (example: Rose Family—apples, pear, peaches, plums, etc.) can be strategically placed on a sturdy stock (Rose Family). It would be possible to reproduce several varieties of fruit, all strategically placed on that stock to allow a "checker-board square (all fruit of a certain variety) facing along lines for harvest. The farmer would harvest the crop of plants facing into a row on both sides of the trees. The next maturing crop would be on another ninety-degree direction depending on the sun and shade requirements of each species on the root stock. This would allow the production of at least four varieties of fruit from the rose Family to be harvested depending on the maturation of the fruit. Apples, pears, peaches, plums, etc. All have different maturation times and the same stock used to impregnate each of the species would make that rootstock more productive. The same care (fertilization and pest control) would only be given to one plant while producing four different Species, varieties etc., from the same plant. As described several varieties from the same species may be harvested from the same root stock if maturity of the varieties will not interfere with pollination.

The same process can be used for stocks from other fruit or nut bearing Families and species. The production of these varieties en masse at an almost exponential rate would provide an industry with a prolonged season with the same care of only the standard number of plants. It would be advantageous to back yard gardeners to have a season-long production of fruit from the same tree.

The technique for introduction of the undifferentiated parenchyma from each individual stock would be less time consuming than the present method of introducing an already vegetative active branch from an existing plant. The method will be to make an incision on the sturdy stock in each of the areas where the specific variety will be positioned and introduce the undifferentiated cells with the necessary nutrient mix and patch.

Most plants will reproduce new growth if a limb is severed. There is reproduction of parenchyma cells at or near the severed limb ant the undifferentiated cells reproduce a new limb with all the characteristics of the missing limb. The new limb will follow all the rules set by that plant for a gravity environment, including the production of undifferentiated cells spontaneously in normal gravity when new growth or trauma occurs. New undifferentiated cells can be introduced at such sites or be artificially induced to provide the same results.

If the union of pollen and ovary for a plant occur in a weightless state, the plant would not have any instructions to reproduce anything but undifferentiated cells (parenchyma). The use of apical undifferentiated cells may produce the same results in regard to exponential growth of cells for purposes of harvesting undifferentiated tissues and that tissue can be replicated at an almost exponential rate.

Specific varieties can be selected for the use as scions. The amount of a new variety produced in zero gravity can be enormous, and provide a load-time of the introduction of a new variety by years. The use of this technology for plants, especially woody plants with a long reproductive cycle could be tremendous considering the long time frame between discovery of a new variety, etc. of a plant and introduction to the industry. This is especially important in the efforts to save endangered plants or when a need for a massive number a specific species is required for the detoxification of a region (radiation, etc.) is required.

The time between the discovery of a new and remarkable variety of a plant and the market place for plants can vary based on the life cycle of the plant. There are exceptions such as herbaceous plants like tomatoes that can be reproduced by seed and self-pollinated using standard processes without too much of a problem. However, woody plants that have life cycles that may be years long cannot be reproduced in any numbers and consequently the timeline for introduction into the market place may be years after discovery. When a plant that has a unique property (including endangered species) and has a reproductive cycle that may be more than a few years the use of zero gravity become evident. The seed or the use of pollen with an ovary may be an optimum vehicle in spite of being exposed to gravity during formation and needs to be studied because any material transported to zero gravity may have already been exposed to the elements that will prevent cell reproduction of the primordial cells in bulk. The undifferentiated cells from a growing plant placed in a weightless environment may be one of the sources of undifferentiated cells that can reproduce in an exponential fashion. The cells in the primordial tissues or undifferentiated parenchyma of apical meristems can be redirected to the replication of the undifferentiated cells in a manufacturing process.

Animals

The current method of harvesting stem cells for a useful purpose in animals is complex. The use of all relatively non-differentiated tissues from after birth has become the only source of "stem cells" under that definition. It is known that even such tissues have merits. Problems involving the "harvesting" of the placenta and related tissues obtained from humans and distribution of such "refined" tissues using the current state of the art have become a political issue because the stem cells harvested are programmed in a genetic sense to become zygotes (new beings).

All mitosis in an Earth-bound reproduction will lead to reproduction of cells leading to a zygote and beyond. Current methods of obtaining stem cells include using the unborn, the placenta, and forcing a further reproduction of such cells. This procedure usually ends with the straining of "stem" cells in a selective method based on the molecular size of a zygote versus a more advanced cell that can be eliminated based on size produced in a gravity environment. There are no real quality assurances with such a procedure. Reproduction of pure undifferentiated stem cells on a commercial basis is not available in a gravity-based system.

There is an ethical question regarding a "formed" animal zygote versus the use of undifferentiated cells that cannot reproduce into an animal unless there is an intervention that would require extraordinary steps to produce an animal. The cells produced in a weightless environment will not be used for reproduction (although theoretically possible) during this process and will be manufactured for the purpose of saving, preserving and healing animals (including man). The cells will be single cells without any direction on production of an individual or even a specific organ. Undifferentiated tissues re-construct the cells in plants and animals continuously until death. The use of pure undifferentiated cells for the purpose of healing tissues is a gift for animals, including man. Creation of the "perfect" animal is not an objective, but should be carefully monitored.

The method of reproduction of animal cells at mitosis will be in regard to current practices. The process must be modified to take into account that the cells will be reproducing in a three-dimensional environment. Current practice only allows for a two dimensional expansion. The container for the expansion of the cells produced, storage and other manufacturing concerns will be addressed. Cells that reach telophase of mitosis will continue to expand in numbers (exponential) and can be confined, exuded through a special process, preserved (including suspended animation) and packaged for distribution in an efficient manner through the use of robotics. The present method utilizes the current technology for the extraction and reproduction to provide a mechanized system for the manufacture of primordial or undifferentiated tissues from both plants and animals (including humans) in zero gravity.

The present invention also encompasses a method of producing stem cells comprising obtaining purified stem cells from an embryo of new-born animal and culturing said stem cells in a weightless condition or environment resulting in the cell replication of identical stem cells. Further included in the present invention is a method of producing undifferentiated cells from an animal, such as cells from liver, kidney, heart, skin, and other cells from the animal body including organs for the purpose of replication of undifferentiated cells including obtaining the undifferentiated cell from the animal, and culturing the undifferentiated cell in a weightless condition or environment resulting in the cell replication of identical undifferentiated cells. Additionally, the undifferentiated cells may be a subcutaneous skin cell obtained by harvested from the animal, wherein the culturing results in near exponential replication the cells overtime.

Further, the present invention encompasses a plant or animal or undifferentiated cell thereof produced by any of the methods described herein and in any of the priority documents, wherein said plant, animal or undifferentiated cell thereof comprises at least one identified gene that has a change in expression level as compared to the gene expression profile of control cell, wherein the identified genes are associated with adaptation to the hostile environment.

More specifically, the egg and sperm are united using standard in vitro fertilization (IVF) techniques for harvesting human or animal eggs, collecting sperm and inseminating the egg with the sperm in a laboratory dish in IVF culture medium. The dish is then placed in an incubator at a controlled temperature which should be the same temperature as the female species' body. It generally takes 18 hours for fertilization of the egg to be complete.

If the fertilization or the union of the egg and sperm occurs in weightless conditions then the single fertilized cell can be maintained in the incubator with the change of medium over time. If the fertilization occurs in a gravity condition or environment, then after fertilization is complete, and before the fertilized egg or zygote divides, the fertilized egg should be immediately transferred to a weightless condition for culturing. However, if there will be a delay until the culturing in weightless conditions can occur, the fertilized egg should be placed in suspended animation before it divides into two cells, such as freezing the egg. At a later time, when the fertilized egg or zygote can be cultured in a weightless environment, it should be revitalized from its suspended animation, and cultured under the conditions to expand the fertilized egg into a culture of undifferentiated stem cell using known stem cell culture techniques that a publicly available in scientific publications, patents and by disclosed on-line methods and media.

For example, a medium useful for the isolation of embryonic stem cells is "ES medium." ES medium consists of 80% Dulbecco's modified Eagle's medium (DMEM; no pyruvate, high glucose formulation, (InVitrogen or Signma), with 20% fetal bovine serum (FBS; Hyclone), 0.1 mM β-mercaptoethanol (Sigma), 1% non-essential amino acid stock (Sigma or other known sources). Preferably, fetal bovine serum batches are compared by testing clonal plating efficiency of a low passage mouse ES cell line. FBS batches must be compared because it has been found that batches vary dramatically in their ability to support embryonic cell growth, but any other method of assaying the competence of FBS batches for support of embryonic cells will work as an alternative. But any known media for culturing the replicating stem cells can be used and tested by the scientists performed these experiments to select the appropriate medium to obtain optimum results. Appropriate plant cell culture media known to skilled persons can be selected to culture undifferentiated plant cells according to the present invention.

The cells are cultured in 3-dimensions by simply suspending the cells in a closed culture vessel in the weightless environment which will keep the cells suspended without the need for any agitation as the cell will not settle to the bottom of the vessel that they would in a gravity environment. Any know methods of 3-dimensional cell culture can be used to culture the replicating undifferentiated stem cells, which could include culturing methods from Mina Bissell's laboratory, such as for example disclosed in *J. Cell. Sci.*, 2003 June 15; 116(Pt 12):2377-88.

Somatic embryogenesis has been the model for mass clonal propagation of a diverse array of higher plants, and also a model for studies of embryo development and cell differentiation. For certain species, differentiation into somatic embryo requires cells to undergo a transitional stage, whereby embryo-like structures are formed. These embryo-like structures are comprised mainly of undifferentiated parenchyma cells. The conversion of these structures into embryos is regulated by a number of different genes under normal conditions. However, when submitted to microgravity conditions, the cells in embryo-like structures may behave differently. The principal objective of the experiments of the present invention is to evaluate whether cells of a monocotyledonous and a dicotyledonous plant develop normally from the transitional stage into normal somatic embryos under space (microgravity) conditions. Histological (structural) and genetic analyses will be performed to assess the cells.

Additionally, suspension cultures have been widely used for tissue culture and mass clonal propagation of a diverse array of higher plants, and also as models for studies of cell development and differentiation. Analysis of these cells will verify structural and genetic changes in plant cells submitted to the effects of microgravity. In addition, cell growth and replication will be assessed visually. Structural changes will be performed through histological analyses, including light microscopy, transmition electron microscopy (TEM), and if feasible, scanning electron microscopy (SEM). Genetic analyses will be performed to evaluate differential gene expression under microgravity.

Material and Methods
Plant Material:
  Monocotyledonous model species: *Encyclia plicata*, an endangered orchid
  Dicotyledonous model species: *Arabidopsis thaliana*, a small flowering plant that is widely used as a model organism in plant biology and its genome has been completely sequenced, providing extensive genetic and physical maps
  Dicotyledonous model species: *Caesalpinia pulcherrima*, a tropical flowering tree.
  Dicotyledonous model species: *Tabebuia aurea*, a tropical flowering tree.
Ground Cell Suspension Initiation:
  Cell suspension cultures are initiated for all species above mentioned, using callus tissue. Callus is comprised of undifferentiated parenchyma cells, with no pre-determined growth pattern.
  For the orchid suspension cultures, the MS culture medium (Murashige and Skoog, 1962), modified with 1 mg/L 2,4-D (2,4-dichlorophenoxic acetic acid), an auxin, and 0.25 mg/L 6-BA (benzyladenine), a cytokinin is utilized. Cultures are multiplied and built up in 125-ml Erlenmeyer flasks, under agitation in an orbital shaker at 109 RPMs. *Arabidopsis* and tree c ell suspensions are cultured on MS medium modified with 1 mg/L 2,4-D. Once a significant amount of cells are produced, they are transferred to 10-ml opticells. Also WPM (woody plant culture medium) medium (Lloyd and McCown, 1986) modified as the MS medium above may be used for woody species of plant.
  OptiCell™ is a sterile, sealed cell culture environment between two optically clear gas-permeable growth surfaces in a standard microliter plate-sized plastic frame with specially designed ports for access to the contents. OptiCell allows an ideal environment for cell growth, microscopy, treatment, selection, separation, harvest, storage, and shipping. Optically clear gas-permeable growth surfaces allow diffusion of oxygen and carbon dioxide for optimal cell growth and permit microscopic examination at any stage of any cell process. OptiCell is compatible for use with standard, phase contrast, confocal, and high-resolution time-lapse video microscopes and takes up a fraction of the space of conventional cell culture devices. Access ports allow aseptic access to the interior and its contents.
Space Hardware:
  Each opticell contains about 10-12 ml of cell suspension. Opticells are maintained in quiescent conditions for both ground and space environments and are evaluated periodically through visual observations for cell growth and development. Under microgravity (space) conditions, opticells are arranged in a C-Hab hardware developed by Bioserve, University of Colorado, comprised of 6 individual Opticell cell culture systems, peristaltic pumps and a control circuit board. The C-Flab hardware allows the transfer of 1 ml of suspension from one opticell to the next during transfer of cells to fresh medium. An aluminum base and an extruded aluminum outer box with a clear optical window provide the second level of containment. Visual evaluations in space are performed with the aid of video cameras. The C-Hab is associated with CSI camera modules. Each of the camera modules contains up to three analog color video cameras, fitted with either microscope adaptors or standard lenses for macroscopic view. This allows the observation of cell growth and replication throughout the period of experimentation in space. Still images (jpegs) are fed to the ground periodically during the entire period of the experiment, thus generating a time lapse for cell growth and replication. The hardware and related control software are tested and evaluated previous to launch.

Evaluations of Cell Suspensions:

Samples from suspension cells maintained in opticells, under both ground and space conditions are collected and compared for histological and genetic analysis:

1. Histological analyses: Cell suspensions are prepared for light and electron microscopy. Opticells are compatible for use with standard, phase contrast, confocal, and high-resolution time-lapse video microscopes. Cells are examined microscopically on either optical growth surface or in between. Oil immersion lenses (up to 100×) are used on the membrane without disruption or contamination. The membrane is sectioned for small scale staining and microscopy. Additional samples are removed and fixed in Glutaraldehyde for subsequent evaluation of cell ultrastructure through TEM and SEM. These analyses are performed for all species.
2. Genetic analysis: Gene expression analyses is performed to evaluate possible genes that are either turned on and/or off under microgravity. Suspension cultures maintained in space are fixed in RNAlater (Ambion) liquid preservative through the Kennedy space center fixation tube (UT), hardware designed to provide proper containment of fixatives for biological samples in space placed inside the C-hab environment. RNA is isolated and compared for both ground and space suspension cultures to evaluate gene expression. Molecular biology techniques for reverse transcriptase polymerase chain reaction (RT-PCR) and/or copy-DNA amplified fragment length polymorphism (cDNA-AFLP) and gel electrophoresis according to standard known techniques are used for gene expression analyses in ground (TREC lab). Microarray analysis of gene expression is performed.
3. Additional evaluations: Preliminary experiments in ground environment (on earth as opposed to in space) are useful to address details and to generate practical solutions for the successful establishment of experiments in space. Evaluations for both earth and space experiments provide additional information and data specific for the Opticell cell culture system environment and include specific conditions for the opticell cell culture system environment, such as cell growth rates, cell densities, subculture frequency, and size and condition (live vs. fixed) of samples for histological and genetic analyses.

Experimental Design and Statistical Analyses:

Controls are comprised of 10 ml of suspension cultures maintained in 6 opticells under ground-laboratory conditions. Treatments are comprised of 10 ml of suspension cultures maintained in 6 opticells in microgravity. The C-Hab environment has been accommodated into modular racks inside modules provided by Spacehab, placed in the Space Shuttle Endeavour, launched on Aug. 8, 2007, Mission STS-118. The experiment ran for a period of three months approximately, whereas the controls are maintained in ground and the treatments are maintained in the International Space Station (ISS). Treatments were returned to ground through another space shuttle mission on Nov. 8, 2007. Analysis of Variance (ANOVA) are performed using SAS statistical package for analyses of results. Means for treatments will be compared for all parameters evaluated using the Tukey's test.

Data were collected regarding plant growth characteristics and the results of these studies showed that the cells grown in the weightless environment on the ISS replicated to a greater mass than the control cells grown in a laboratory under the earth's gravity with all other culture conditions the same. One of the two tree species demonstrated significant growth on orbit in the weightless environment as compared to the ground controls.

The studies support that cells would replicate rather than duplicate and that exponential growth of the cells will occur as long as the undifferentiated cells are nurtured and maintained in a weightless environment. The results show that that cell growth on the ISS in three of the species of plants demonstrated higher growth than the controls on Earth. The third experiment (Moncot—orchid species) was contaminated with a yeast infestation and is being examined to determine the species and information regarding gene expression and replication.

Effect of Weightless on Growth of Replacement Cells in Visitors Maintained in a Weightless Environment As noted above, there have been reported studies of humans who lived in a weightless environment, such as on the Space Station, that show that these individuals lost body mass during their time in this weightless environment even though these individuals exercised during their stay in this weightless environment. In a weightless environment, even established cells produce undifferentiated cells immediately adjacent to the existing cells that "mimic" the cell, but do not perform properly and do not produce the tissue of origin (bone, brain). The tissues that have the greatest amount of circulation will be effected first, such as blood and brain, and these tissues will be compromised. All long term orbital and interplanetary missions should take under consideration the loss of body mass regardless of the precautions incorporated into a space mission, including exercise, supplements and the like to maintain body mass. The rule concerning exercise in a weightless condition may be harmful because of the degradation of the body and replacement of the destroyed cells by a cell that will not be a replicate of the original cell. The cell reproduced in normal cell reproduction in one "G" does not have the influence of the one "G" and replicates into a "K" cell which functions, but is not the replicate needed for normal function in the tissue. For example, a new cell in a muscle tissue should function as a normal muscle cell but it does not.

All long-term missions should be reconsidered until there is an evaluation of this concept and examination of the information presented herein regarding the formation of non-differentiated cells and unlimited reproduction of such cells. Thus, the risk to individuals who spend any extended time in a weightless environment is based on the premise that undifferentiated tissues can reproduce as "pure" undifferentiated cells produced by a male and female union in weightlessness.

The effects of long-term exposure to weightless conditions is governed by the knowledge that the reproduction of existing cells in a visitor will not be faithfully reproduced to provide replicates of the generating tissue. Not wishing to be bound by a specific theory, the present invention is based on the theory that the cells that continually are produced do not form into tissues (bone, muscle, blood), and will not develop or mature into the differentiated cells from the original cells. The cells will not differentiate properly into the parental cell, but under the weightless environment will form a cell not functional to the specific task intended for the cell, such as bone, muscle or blood. The term "K" cell' is only a designation, but is being used herein to describe a cell not yet studied, but present in all long-term space visitors.

In an effort to solve the loss of body mass in weightless environments, the experiment concerning the use of embryonic tissues in the "South African" experiment confirmed the theory that the reproduction of new cells does not follow a normal growth pattern. The tissues derived from animals within hours of lift-off in Russia provided information concerning the techniques that may be used in future missions. The South African mission did provide information including the reproduction of tissues in a weightless environment NOT reproduced with a sperm and egg in zero gravity, or a "new" seed or egg of a plant recently pollinated. The expansion of cell growth did not take on the normal pattern and instead became an unrecognized pattern. Again, the experiments provide information that lead to the confirmation of the theory that all cells derived from tissues in weightless environment are not orientated to reproduce the same type of tissues adjacent to those tissues.

The cells reproduced in likely become "inert" cells meaning that the cells do not have the same specialized function as the adjacent differentiated cells in the tissue from which these cells originate and are reproduced. In other words, the longer an individual stays in space, the higher the probability that the body will degrade, and may do so at a higher rate in the individual who stays in a weightless state. In fact, such cells may be anaerobic in character and pose a future cancer risk since the cells do not follow the "Krebs cycle," resulting in fermentation rather than an aerobic cycle.

Individuals in orbit weightlessness have been experiencing loss of bone and muscle mass, and other tissue. The areas of the body with the least amount of circulation (bone, muscle, tendons, fat,) will experience the most trauma because of the circulation to those areas of the body.

Intense exercise in zero gravity has not been able to slow the loss of tissues from the body and may be counterproductive to long-term intact cell survival, since cells are created and destroyed at much higher rate. It is known that the body is reproducing new cells on a continuous basis and the more exercise is performed, the more cells that become exposed to the reproductive process and the more undifferentiated cells that are produced. The reason for the loss of mass in the bone, muscle and other tissues is that the reproducing primordial (stem) cells that do not have a direction (bone vs. muscle, etc) die or form a cell we are not familiar with unless we look. A lock at the space traveler in a weightless environment without the proper devises to allow for an artificial gravity may create a major problem.

Given that the human body continuously reproduces specific differentiated cells for each organ and that such cells may only be primordial with no direction, there is a strong possibility that the primordial or undifferentiated cells do not develop into the differentiated tissues intended (such as bone, muscle, or other specialized cells) and may degenerate or possibly form a cell that we are not familiar with in the reason of normal thinking. It is known that there is a loss of tissue and all orbital and interplanetary visitors should be examined for necrotic or other cells in the areas of the body that have low growth, including the brain and other organs studied.

Many technologies have been applied, including vigorous exercise, to slow or prevent this loss of tissue. The latter may in fact be harmful, since exercise promotes the life and death cycle of cells, and death of the cells does occur, but the new cells produced are undifferentiated with no program to produce the differentiated cells which they are to replace. Even the new reproductive tissues of visitors become undifferentiated when produced and either transform into the tissue itself (with a "lag" time) into the bone, etc. or die or become an "inert" tissue with no specialized function.

On-Orbit Manufacturing Facilities for Stem Cell Production

The use of an on-orbit manufacturing facility or "wheel" in space using new technology will allow production of primordial or undifferentiated cells and tissues from plants and animals and provides an environment for those that harvest the cell crop (FIG. 1).

The reproduction of the original cell obtained from the union of the sperm and egg in animals or the pollen and ovary in plants occurs in a 3-dimensional fashion in a culture vessel or container, since no gravity is involved, the cells will replicate and remain in suspension floating in the media in the culture vessel. The cells will continue expanding in the culture vessel until the "yoke" of the process is expended until the size of the cell population has reached its maximum capacity in the container. Then, the newly formed cells can be transferred or exuded from the culture vessel into a container that will provide a suspended animation system for storage and shipment to Earth. A system will be described for the manufacture of undifferentiated tissues in a weightless site, and the cells will be cultured in the weightless chamber in the on-orbit manufacturing facility shown in FIG. 1 or in a similar type chamber in another space vessel or station.

Manufacturing

Capturing the reproducing cells from plant and animal primordial tissues will be a mechanized procedure. Cells (individual or two or more) can be captured and pulled through a mechanism to encapsulate the cell(s) in a sheath that mimics the cells walls of single celled organisms such as bacteria. The storage of the undifferentiated encapsulated cells must be stored in a weightless system where the metabolism and physiology of the cells proceeds into a state of suspended animation. Temperatures and storage conditions can be adjusted to provide an optimal condition that allows the harvested cells to be stored. Slam freezing is used to preserve semen specimens for cattle now and can be used. The process of the cells must be slowed to a level that will allow storage and eventual handling of the cells when returned to a gravity environment.

Yeast may represent a model for replication of both plant and animal undifferentiated tissues since yeast provides the preparation (substrate), innoculum (undifferentiated cells and/or tissues), cultivation (providing ideal conditions), harvesting (separation of cells from the process), cooling and storage of the harvest at temperatures not to interfere with gravity.

The aerobic respiration (presence of O2) expected in the culturing processes with both plants and animals will be interfered with by anerobic respiration (lack of O2) due to the containment of the production and the difficulty of feeding the entire nutrient system with adequate oxygen, especially near the end of the exponential growth phase of the manufacturing process. Aerobic respiration has both the substrate level and oxidative phosphorylation while anerobic respiration has only substrate phosphorylation. Both use hexose as a fuel (glycolysis). A problem in the manufacture of the undifferentiated cells is that during the anerobic respiration expected in the process, the final electron acceptor through alcohol will be other organic molecules such as pyruvate, acetaldehyde, etc. that will be toxic to the total mass of undifferentiated cells. In the aerobic respiration, the final acceptor is oxygen and presents no problems.

Respiration resulting from undifferentiated cell replication occurs in both plant and animal cell cultures. The exponential expansion of cells follow a the general guidelines for plants and animals:
1. Sugars (Hexose in plants) is the fuel.
2. Zymase in plants is an oxidizing/reduction enzyme to act as a catalytic agent to covert sugar into labile intermediate products.
3. Animal conversion during the metabolic process follow the same general format (Kreb's Cycle).

Plant Model

The expansion of the cells will produce by-products depending on the oxygenation of the system but in containment, both aerobic and anerobic respiration will take place at the same time, producing toxic substances:

Equations:

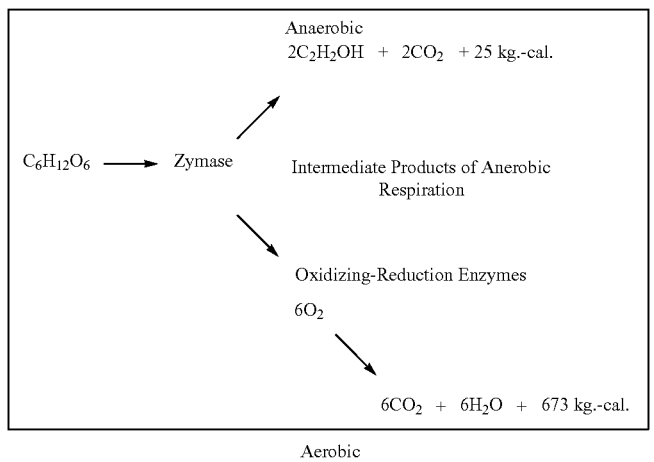

Aerobic

The amount of byproducts accumulates and alcohol with aldehydes, etc. requires removal from the manufacturing system through the use of filters.

Figure 2:
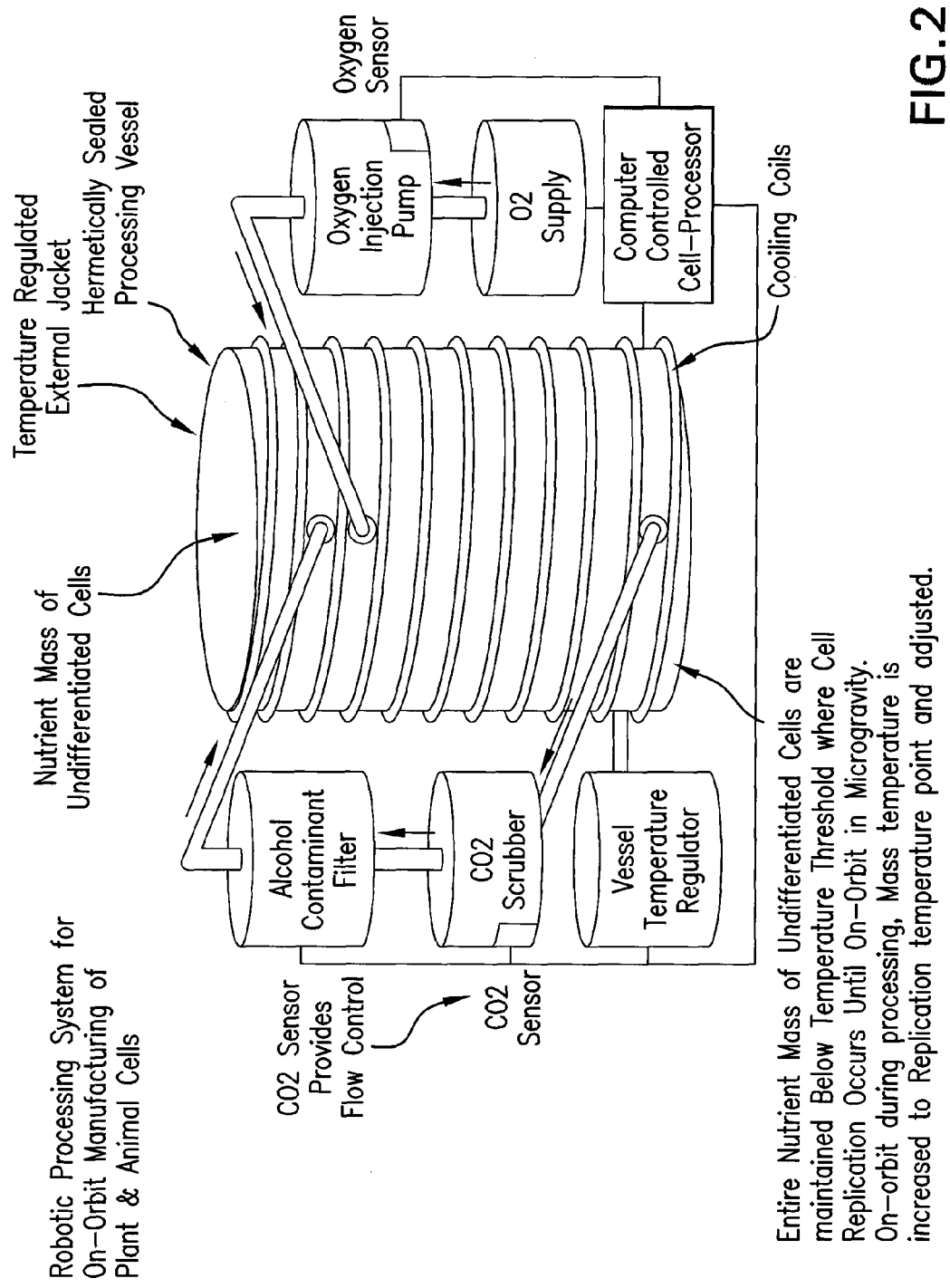

The production of undifferentiated cells requires the filtering of the toxic byproducts and the injection of oxygen into the system. The production of cells requires careful consideration of the "critical mass" determined by the maximum numbers of cells that can be produced by the available nutrients, the supplied oxygen and the removal of wastes. A "flow" system is highly probably where a reaction chamber allows a mix of the nutrient, "seed" undifferentiated cells and oxygen can produce a continual flow of the nurtured "seed" cells with a proper oxygen environment would expand into a container vessel that has environmental controls. However a more simplistic model is useful that can be well-adapted to a robotic system, for example, such as disclosed in FIG. 2. The configuration of the system and its manufacture for each container is based on the following parameters:
  1. Volume of reactor
  2. Amount of substrate (sugars).
  3. Amount of innoculum required.
  4. Filter system for toxic byproducts
  5. Injection of Oxygen
  6. System for cooling reaction during progression of reaction and cooling for storage If the efficiency of the "Volatiles Filter" proves to be inefficient, a separator may be necessary in the system. The manufacturing unit is preferably designed toward robotic manufacturing with the following considerations:

1. The manufacturing unit is at a pre-determined size to contain the initial substrate and also serve as the storage unit for the processed cells return to Earth.
2. The substrate environment is carefully monitored for parameters that will insure a proper environment for the injection of undifferentiated cells (or tissues) into the substrate.
3. An oxygen injection system that provides levels of oxygen to keep the process aerobic and evenly distributed within the nutrient.
4. A re-circulation system with a exit into a filtering system for removal of toxic volatiles also assists in the distribution of oxygen. The system is preferably designed to prevent any high movements of nutrients and cells to maintain a "non-gravity" condition.
5. The exponential expansion of the undifferentiated tissues will cease because of the amount of nutrient, size of the container and/or
6. The toxic materials that may result.
7. The unit can then be reduced in temperature to below the level required for respiration and shipped back to Earth.

The payload of undifferentiated cells will be retrieved much like the Get-Away-Special Program in the 1980's and the SpaceHab system and replated with another "factory" Such factories can replicate the primordial or undifferentiated cells and tissues of both plant and animal on a commercial scale. The advancement in technology will allow for better efficiency with each mission.

Production

The primary cells used to replicate identical cells in weightlessness will produce cells in an undifferentiated state much like a "seed" in crystallization in minerals or supersaturated solutions. Biological processes may follow different patterns, but the replication of the seed cell will produce undifferentiated cells in an exponential fashion. Therefore, there is a need for a device to control the replicated "seed" primordial tissues to produce encapsulated cells.

Biological "factories" such a female termites can be used as model for the replication in zero gravity. The primordial tissue in an exponential explosion needs to be controlled as with the queen termite. The process involves the direction of the undifferentiated tissues through a processing chamber where a protective coat is applied. The process would allow a continuous flow of the primordial cells into the encapsulation process. The cells would then be directed into a chamber that is designed to provide a conditioning process for processing the cells into a state of suspended animation. The processing of the undifferentiated cells can be conducted using current technology with modification known to persons skilled in the art of cell culture and manipulation. Use of ultra-light components of a non-metallic nature may be essential to provide not only a gravity force, but also an electro-magnetic influence. Containment of the production in a shielded environment to protect the production and maintain the sterility of the cultures will be necessary.

Selection of the egg and sperm is of great importance. The animals must be selected to provide the egg and sperm at an early age. The break down of the genetic code in latter years is well known for both egg and sperm Even the generation prior to the donors must be considered. The telophase of mitosis of the union of the egg and sperm will provide stem cells for the individuals in a particular blood type and other tissue matching characteristics to match the donor with potential animals of like character. Banks of eggs and sperm in the case of animals (including man) and pollen, plant female organs and undifferentiated cells, such as parenchyma can be stored in suspended animation for future generations. It is expected that individuals will "bank" sperms and eggs in the early years of their sexual years to insure the capability of regenerating or even replacing body parts. The bank of sperm and eggs can be held in suspended animation. If a situation arises where there is a future need for stem cells, the "pure" stem cells will be available.

The present invention comprises the methods and facilities so that pure stem cells can be reproduced in a factory mode. The cells will only proceed to mitosis and will not produce undifferentiated cells so that no embryo will develop from the original single cell. The union of a sperm and egg in zero gravity will not result in the production of a zygote capable of developing into an embryo and then into a normal life form. This premise is based on the observations of maladies that occur to space visitors from both the US and Russia who spend some time in a weightless condition. The present invention is based on the theory that the undifferentiated cells produced by specific tissues (bone, muscle) did not differentiate into the intended differentiated, specialized tissues (bone, muscle) and became necrotic (Reference). The additional non-productive cells produced in a weightless condition did not have the "gravity" message required to reproduce in a gravity environment and are imbedded in the normal tissue and interfere with the "normal" cells surrounding the tissue.

The additional data provided by the South African space attempts also lead to a conclusion that primordial cells (undifferentiated) can and will reproduce in a 3-dimensional fashion. The cells produced were the result of already compromised (by gravity) cells that did indeed reproduce in the 3-dimensional environment. However, the instructions on reproduction (genes) were not only compromised by the union of egg and sperm under gravity, but also lift-off that provided many more gravity forces that certainly migrated the starches, etc and effected the experiment. The production of undifferentiated cells in volume can be achieved using the present technology in a weightless condition.

Design and Function of a Space Craft Using a "Clutch" Technology

The current visitors to space in orbit and destined for other planets are subjected to a weightless environment where extensive documentation points toward degradation of the human body. Long space voyages to Mars, for example would not be practical and even suicidal. A method of providing an artificial gravity has been under study for decades, but docking of a space craft, conducting experiments in weightlessness, and still providing an environment where a simulation of gravity are present have not been solved until now.

The present invention comprises a space craft (as shown by the diagram in FIG. 1) that can be assembled in orbit using a "tinker toy" method of construction using capacity figures for the space shuttle or more advanced vehicles. A puncture-proof inflatable two-piece ("clutch" and wheel) can be put in place around the stationary central weightless chamber. The central "weightless" chamber can be used for docking and experimentation. An adjacent outer segment (wheel within a wheel") is a "Clutch" that will be at neutral or rotate with the outer wheel. The neutral condition will always exist in inner "Hub". The "clutch" can be slowed to "Neutral" and air-locked" to allow the transfer of personnel and/or supplies into the "clutch". The "clutch" system is sealed and begins to rotate to catch up with the outer spinning wheel. Once it "catches" the speed of the outer rotating wheel, it can mate with the wheel and transfer of the personnel can take place. The rotation of the "clutch" allows for transfer from a neutral docking zone and laboratory that allows experimentation in a weightless environment to the outer wheel that mimics Earth's gravity. The wheel may be approximately 100 meters or more in diameter and include at least four to eight "spokes". The vehicle can be "mated" to the existing space station.

The present invention further comprises an electromagnetic "track" system that will interface between the inner capsule (docking, laboratory, control area, and other compartments), the "clutch," and the outer wheel to provide a friction-less interlace. A ball bearing system can be engaged during transfers between the "capsule" (weightless condition), the "clutch" and the wheel during transfer of goods and personnel and act as a back-up for the electromagnetic system. The rotation between the "Neutral (Capsule), the "Clutch" and the "Wheel" can all be interfaced with electromagnets that will allow for the production of electricity.

The present invention additionally comprises a computerized system of weights and balances that are necessary to adjust the entire system. Transfers of personnel and equipment will require a weight and balance to this relatively sensitive system and can be accomplished by pumping fluids or movement of weights in the spokes of the "wheel" to counteract the movement of supplies and personnel to the "rim" of the "wheel".

The present invention also comprises the spokes of the outer wheel that will act as the elevators to the outer region of the wheel and to provide ballast for balance of the system. The "rim" of the wheel will circulate at a speed that creates a centripetal force that will mimic Earth's gravity and allow the inhabitants and plants requires for subsistence to exist in a near-nor mal condition. The "rim" will require adjustment by visitors, but there some individuals that do adapt to such an environment and function. The sleeping "cocoons" can be arranged to allow for maximum benefit of the centripetal force. Plants can also be propagated in such an environment.

The mathematics to calculate the circumference of the wheel to create a near Earth simulated gravity is well known. Examples are given in a publication "Artificial Gravity and the Architecture of Orbital Habitats" by Theodore W. Hall, presented at the $1^{st}$ International Symposium on Space Tourism, Bremen, Germany, 1997 No definitive calculations will allow for a prediction of comfort in a space habitat, but the circumference of the wheel will be determined by the adaptation of individuals to the physical conditions and stamina in such conditions. A selection process may be necessary to determine personnel for such missions.

Providing an artificial environment that mimics gravity is also necessary based on review of the data and understanding the principals of cell reproduction in weightlessness. A space craft traveling at a constant velocity in interplanetary flight will create a weightless environment and be subject to the same science already discussed concerning orbital missions. A "wheel" and "Clutch" arrangement must be incorporated into any vehicle attempting a long interplanetary flight, including a voyage to Mars.

Spacecraft Structures and Electromagnetic Sub-System

The Earth is protected from the Sun's radiation and other particles by the Earth's ionic shield. Mars and the Moon do not have such a field and is cited as a reason for the inability of these bodies to maintain life on our scale. The Earth's ionic shield is the result of the expulsion of a positive charge from the Northern polar region that forms a electromagnetic force that forms a spherical force field covering the planet and terminating at the Southern polar region. The system that provides the electromagnetic shield is powered by the motion of the various metals (primarily Iron) in the heated core as described by current science.

The present invention further comprises the space craft described herein which will have a abundance of electrical power developed by the interface of the "clutch" system using simple electromagnets. The weightless inner portion of the hub must remain stable for the purpose of the docking of a visiting space craft, experiments, and other functions. The "clutch" will also remain in a position adjacent to the main facility. However, the movement of the outer wheel will always provide a field production at the interface of the clutch and the wheel. The continuous electric power produced can be used to produce a electromagnetic field based on the same principles that protect Earth from the damaging radiation, etc. from the Sun. The portion of the space craft providing the positive charge (as the North Pole) will be directed toward the sun and a receiver will be placed at the opposite end of the space craft. The positive charge may be on an extension boon to provide a suitable profile for deflection of harmful radiation and other harmful effects from the Sun. As with Earth as a model, a proper profile for the amount of power required to achieve protection from harmful radiation can be determined. The amount of power to accomplish a protective shield will be low because the power supply at the positive side will be reduced to a certain degree, but retrieved at the negative pole. There are no ground cables in space. The principles that protect the Earth are applicable in space.

Acceleration of Adaptation and/or Evolution

When in a weightless and/or near-weightless environment, typically in space and on-orbit, but also in any and all such equivalent non-weight and weightless circumstances, there exists cellular materials and wherein a process or processes are performed in those environments, specifically in the absence of a "weight-forcing condition" (a circumstance where weightlessness prevails), specific genetic attributes will be altered, i.e., either switched on-from-off or switched off-from-on, and that certain of these gene characteristics may be identified, as to their function and nature, and may consequently and purposefully selected and altered in order to achieve specific, valuable, and useful outcomes, to derive targeted cellular characteristics and accordingly, behavior, performance, and function, and/or that result in the securing, development, and/or enhancement of certain preferable and valuable attributes of said cells, whether as part of a cell, a cellular mass, a cellular volume, or a living organism, in whole or in part.

Wherein these cellular components and sub-components including cellular elements, genes, DNA, RNA, enzymes, hormones, etc., may be tied individually or collectively in structure, process, and function, such that they act to produce characteristics, attributes and capabilities both cellular and when in-complex and mass as may be observed with a living organism or organisms, such that they express living behaviors which include, but are not limited to increased or decreased or modulated metabolic rate, i.e. respiration, transpiration, anabolic and catabolic activity levels or both, up and/or down regulated, increased, decreased, altered or modulated nutrient uptake, increased, decreased, altered, or modulated waste and byproduct output, modification or alteration of water and fluid uptake or release, alteration of structure, i.e., modification, adaptation, or variation of cell wall thickness, structure, or composition, alternation of character as relates to external environmental pH (acid/base) conditions, salinity and mineral presence, ionics and salts, water, temperature variations, both high and low extremes as well as cellular character, performance and viability in the presence of rapid temperature excursions, or combinations of external chemical, thermal, physical, energy, electromagnetic, radiation, solar, vibrational, acoustic, magnetic, paramagnetic, gravitational, weight-forcing conditions. In other words, all external conditions which may affect or interact with the cells, cellular mass or volumes, components thereof, or organisms in whole or in part may be modulated.

Also contemplated by this invention is the alteration of those biological and cellular processes, activities reactions, motions, behaviors, process induced reactions and behaviors and the like which are deliberately conducted or affected or driven or occur in a "zero-weight-force" (so-called microgravity) environment. This includes, but is not limited to, the alteration of genes, DNA, RNA, enzymes, hormones, and all biologics known to those competent in the art of biology and cellular sciences, which result in the creation of and/or development of cellular components, cells, cellular masses and volumes such that they or their complexed resulting cellular organisms, may be altered, modified, and enhanced to yield valuable and useful new cellular types and variant organisms including, but not limited to, cows resistant to mastoid staphylococcus disease, cattle resistant to mad cow disease, wheat resistant to wheat rust, soybean crops resistant to soybean rust, agriculture crops resistant to ralstonia, citrus capable of growing in Northern latitudes, *Jatropha, Camelina*, and other third generation biofuel crops capable of being grown in the Continental US latitudes, citrus resistant to canker and greening, interbreeding of *Tamarix* to overgrown existing invasives in the Western US to eliminate water losses, tailored halophyte production and growth, minimization of waterway invasives through retailoring of hydrilla, water hyacinth and egeria species, modification of grapevines to eliminate grape blight, modification of corn, soy, wheat, rye, rice and multiple other types of food crops enabling them to be grown and viable in drought conditions, in harsh wind and climate environments, or in adverse soils and a wide variety of other biological and cellular and organism modifications, alterations, and restructurings of similar usefulness and value and nature.

The present invention recognizes the value of the accelerated and sustained proliferation or replication of undifferentiated cells from plants and animals in weightless conditions as an opportunity to select for organisms adapted to specific, even harsh, environments. By exposing the proliferating or replicating undifferentiated cells to one or more "non-natural" environmental conditions while in orbit (or weightlessness), one can "force" the cells to express genes that enable the cells to adapt and survive in these abnormal environments. The selected cells can be cultivated to develop into an organism that would be adapted to the specific environmental conditions to which its primordial cells were exposed.

The present invention comprises "replication processes" that occur in a weightless environment as contrasted to the normally occurring reproductive processes that result in progress or development through normal maturation stages and cycles resulting in the differentiation of cells which are known as "reproductive processes" on Earth. However, on orbit in weightless or microgravity conditions, cellular activities occur and are referred to as "replication" which can also be referred to as "duplication" or "proliferation" of copies of cells that are identical in structure and function to their originating predecessors. This process is known as replication and results in an undifferentiated cell replicating or duplicating itself without differentiating into a more specialized cell with a predetermined function. Thus, the process allows for the production of large amounts of undifferentiated plant and animal cells in the weightless or microgravity environment.

As used herein, the term "undifferentiated" means a primordial state of a cell or cells capable of differentiation and proliferation to produce progeny cells that can be physiologically, biochemically, morphologically, anatomically, immunologically, physiologically, or genetically distinct from the primordial state.

As described above, the present invention provides methods of adapting plants and animals to survive in a hostile environment, wherein the method comprises culturing undifferentiated cells from the plant or animal in a weightless condition that mimics at least one element of the hostile environment to which the animal or plant is to be adapted; selecting the cells that proliferate in said condition; and cultivating said selected cells to produce plants and animals that are adapted to grow in that particular hostile environment.

Any suitable means for achieving reduced gravity or microgravity conditions can be used for performing the method. In one embodiment, the method is performed under reduced gravity or microgravity conditions in space, e.g., aboard the Space Shuttle, the Space Station, a sounding rocket, or a satellite. In another embodiment, the method is performed under reduced gravity or microgravity conditions simulated on Earth using a machine or other device suitable for this purpose.

As used herein, the term "hostile environment" is used interchangeably with "non-natural environment" and means an environment in which the plant or animal does not normally exist or survive. By way of example, a hostile environment for a banana plant would be the Arctic Circle. Another example of a hostile or non-natural environment for almost any plant or animal would be the surface of Mars.

Many elements of the particular hostile environment of interest can be chosen as the selection pressure to "force" the undifferentiated cells from the plant or animal to express a subset of genes that will enable them to adapt to the hostile environment. As used herein, the term "force" means to apply a selection pressure to the population of proliferating undifferentiated cells to obtain cells that survive in the condition of interest. Some environmental elements suitable for use include, but are not limited to, temperature, such as excessive heat or excessive cold, high or low concentrations of carbon dioxide, barometric pressure, radiation levels, humidity levels, oxygen concentration, low sunlight exposure, extreme drought, extreme salinity, and the presence of environmental toxins.

In one embodiment, the present invention provides a method of adapting a plant to grow in a hostile environment, wherein the method comprises culturing undifferentiated cells from the plant in a weightless condition that mimics at least one element of the hostile environment to which the plant is to be adapted; selecting the cells that proliferate in said condition; and cultivating said selected cells to produce mature plants, wherein the mature plants are adapted to grow in said hostile environment. The method can be similarly applied to adapting an animal to grow in a hostile environment.

In one embodiment, the method further comprises evaluating the mature plants in the hostile environment. The plants may be evaluated on several criteria including, but not limited to, length of survival, growth rate, reproductive capability, cell structure, and gene expression. Further, the undifferentiated cells that are cultured can be obtained from uniting a pollen and ovule of a plant or a sperm and egg of an animal prior to culturing in a weightless condition or environment or alternatively, can be united in a gravity condition and preserved to be cultured in a weightless environment.

In one embodiment, plants suitable for use in the methods of present invention include dicotyledons. In certain exemplary embodiments, the dicotyledons may include leguminous plants and other large seed dicots, e.g., peanuts, soybeans, common beans, squash, zucchini, peppers, melons, cucumbers and others. Other dicots for use in the invention include potatoes, tomatoes, alfalfa, canola, apples, and pairs. In certain other embodiments, a plant suitable for use in the invention can be a woody dicot, including pome fruits, citrus crops, and vegetable crops.

In other embodiments, plants suitable for use in the methods of present invention include be monocotyledons. In certain exemplary embodiments, the monocotyledons include may include corn ("maize"), rice, wheat, barley, sorghum, rye, banana, plantains, and other grasses.

In another embodiment, the plant may be from the genus *Jatropha*. *Jatropha* is a genus of approximately 175 succulent plants, shrubs and trees (some are deciduous, like *Jatropha curcas* L.), from the family Euphorbiaceae. The hardy *Jatropha* is resistant to drought and pests, and produces seeds containing up to 40% oil. When the seeds are crushed and processed, the resulting oil can be used in a standard diesel engine, while the residue can also be processed into biomass to power electricity plants and jet engines. Thus, *Jatropha curcas* is a promising candidate for future biofuel and energy production. Therefore, expanding the range of habitats in which it can survive is of great interest and importance.

In another embodiment, the organism may be a lichen. Lichens are composite organisms consisting of a symbiotic association of a fungus (the mycobiont) with a photosynthetic partner (the photobiont or phycobiont), usually either a green algae or cyanobacterium. The morphology, physiology and biochemistry of lichens are very different to that of the isolated fungus and alga in culture. Lichens occur in some of the most extreme environments on Earth—arctic tundra, hot deserts, rain forests, rocky coasts and toxic slag heaps.

In another embodiment, the organism may be an algae or fungus by themselves. In other embodiments, the algae or fungus may be associated with other primitive organisms, such as lower plants, including, but not limited to, Thallophytes, Chlorophyceae (for example, green algae, spirogyra, or vaucheria) and Phycomycetes (for example, algae fungi, bread mold, or water mold).

In another embodiment, the undifferentiated cells may be from a plant that has been genetically modified to result in a specific phenotype. There are numerous examples of plants that have been transformed with specific genes so that the resulting transgenic plants exhibit a particular characteristic, such as resistance to a particular pathogen or increased size of fruit. For instance, herbicide resistant plants as disclosed in U.S. Pat. No. 7,169,970, plants that have enhanced nitrogen assimilation as disclosed in U.S. Pat. No. 6,107,547, and tomatoes with a delayed ripening phenotype as disclosed in U.S. Pat. No. 5,952,546 are just a few of the various examples of genetically-modified plants that have been created. Undifferentiated cells may be obtained from any of the many varieties of transgenic plants for use in the methods of the present invention.

In some embodiments, certain plant species known to be suitable for use as biofuels may be modified, tailored, altered, enhanced, by on-orbit, weightless processing of the cells and/or cellular components, such that higher-energy by weight or by volume biofuel product may be produced from said plant seeds and cultivars, and that these species may include the known, 1st, 2nd, 3rd, and 4th generation biofuels, including but not limited to corn, soy, sugar cane, sugar beet, sweet sorghum, maize, palm, pinnata, switchgrass, rapeseed, miscanthus, hemp and other known suitable biofuels of the 1st generation, as well as *Jatropha* (as described above), *Camelina, Manihot*, and algae, including in particular marine algae, as third generation biofuels, including halophytes, particularly *Salicornia*. This embodiment further contemplates modifications, alterations, and optimizations of these biofuel species as a result of weightless (microgravity) cellular processes executed in the zero-force weightless environment on-orbit, as claimed herein, that enable and result in the production of useful and valuable genetically altered and tailored biofuel and crop outputs and end-products.

Methods of obtaining undifferentiated plant cells are well known in the art. A mass of undifferentiated plant cells may be obtained by aseptically removing a small piece of plant tissue from a selected organ, such as from the root, stem, etc., and placing it in a sterile medium containing appropriate nutrients. Such a tissue explant will grow and proliferate into a large number of the same type of plant cells or of related plant cells, without specialization of these cells to form specific plant organs such as roots or leaves, etc. These cells may be referred to as a heterogeneous population or colony of undifferentiated plant cells comprised of single cells as well as aggregates of cells. This type of uninterrupted cell growth and multiplication without the formation of specific plant organs is known as undifferentiated cell growth.

In one embodiment, the undifferentiated plant cells to be used in methods of invention may be obtained from the undifferentiated parenchyma from the apical meristems of the plant. Reproduction and use of apical cell reproduction has greatly increased the numbers of plants in a vegetative reproduction process. The process depends on the isolation of the reproducing cells at the tip of a plant or plant part (root, branch, etc.) known as the meristem and successful cloning of the limited number of cells at the undifferentiated stage of development at the tip of the plant or other actively growing portions of the plant (root, cambium, etc.). Suspension cultures of undifferentiated cells may be prepared from meristem isolates.

Alternatively, the undifferentiated plant cells suitable for use in the methods of the invention may be obtained by proliferation or replication of diploid cells formed by the union of pollen (sperm) and ovule (egg) from the particular plant species of interest under weightless conditions as described herein. It is possible to replicate and produce undifferentiated parenchyma resulting from the unification of pollen (sperm) and egg (ovary) in plants that are unified on Earth, preserved prior to any division of the united single cell, and transported immediately to orbit for the purpose of producing undifferentiated cells capable of replicating identical cells for production of tissues used for parts of plants, and the plant itself, including, but not limited to stems, roots, flowers, seeds, fruits, and other tissues. The union of pollen and ovary (egg) in zero gravity will produce a cell that will go to mitosis and then reproduce that cell continually en masse or until a genetic break down in the cell(s) may occur that would disrupt the exponential reproduction of the same mitosis. The newly formed cells can subsequently be used in the methods of the present invention.

The following example outlines an experiment for adapting a species of citrus plant to grow in colder climates. This example is for illustration purposes only and in no way limits the scope of the invention. As described above, various types of plants may be used in the methods of the invention. Similarly, many different elements of a hostile environment may be used as selective pressures to adapt the plants.

Example—Method of Adapting a Citrus Plant to Thrive in Cold Climates

Suspension cultures have been widely used for tissue culture and mass clonal propagation of a diverse array of higher plants, and also as models for studies of cell development and differentiation. Analysis of these suspension cultures determine structural and genetic changes in undifferentiated plant cells submitted to the effects of environmental elements, such as abnormal temperatures. In addition, cell growth and replication are assessed visually. Structural changes are performed through histological analyses, including light microscopy, transmission electron microscopy (TEM), and if feasible, scanning electron microscopy (SEM). Genetic analyses is performed to evaluate differential gene expression under the specific environmental condition.

Cell suspension cultures are initiated for a variety of citrus tree (e.g. *Citrus sinensis*) that has superior fruit, but is not cold tolerant below 28° F. Cultures are prepared by excising the undifferentiated parenchyma cells from the apical meristems of the plant about one day before space shuttle launch. The cell suspensions are cultured on MS medium modified with 1 mg/L 2,4-D. Once a significant amount of cells are produced, they are transferred to 10-ml opticells and cultured as described above.

On orbit, in the opticells the experimental cell suspension cultures are subjected to temperatures of 25° F. for a predetermined period of time, such as for several weeks or about three months or more on the International Space Station (ISS). Also on orbit, corresponding control cell suspension cultures would be exposed to the optimal growing temperature for that species of citrus. Cells exposed to each growing temperature would be returned to Earth and a portion used for further analyses (see below). The other portion would immediately be separated into individual cell containers with agar and cultured to determine which cells survived. The cells that survived can be nurtured to mature trees and then subjected to temperatures of 25° F. to determine the level of cold tolerance achieved. Other parameters of the mature trees would also be measured, including yield of the trees, length of survival, and growth.

Samples from suspension cells maintained in opticells, under both experimental (25° F.) and control (greater than 28° F.) temperature conditions are collected and compared for histological and genetic analysis. For histological analyses, cell suspensions are prepared for light and electron microscopy. Opticells are compatible for use with standard, phase contrast, confocal, and high-resolution time-lapse video microscopes. Cells are examined microscopically on either opticell growth surface or in between. Oil immersion lenses (up to 100×) are used on the membrane without disruption or contamination. The membrane is sectioned for small scale staining and microscopy. Additional samples are removed and fixed in glutaraldehyde for subsequent evaluation of cell ultrastructure through TEM and SEM.

By the term "control" or "control cells" or "microorganisms" within the meaning of the present invention, is meant cells or microorganisms grown on earth or in a gravity environment as compared to the cells or microorganisms grown in a weightless or microgravity environment as described herein or on the Space Station. Additionally, control or control cells or microorganisms can also mean those cells or microorganisms grown under a normal non-stressed environment, as compared to the stress environment factors and stimuli, as set forth herein.

Gene expression analyses are performed to evaluate possible genes that are either up-regulated or down-regulated in response to the colder temperature. Suspension cultures maintained in space are fixed in RNAlater (Ambion) liquid preservative through the Kennedy Space Center fixation tube (UT), hardware designed to provide proper containment of fixatives for biological samples in space placed inside the C-hab environment. RNA is isolated and compared for suspension cultures in both temperature conditions to evaluate gene expression. Molecular biology techniques for reverse transcriptase polymerase chain reaction (RT-PCR) and/or copy-DNA amplified fragment length polymorphism (cDNA-AFLP) and gel electrophoresis are performed according to well-known techniques to those skilled in the art and are used for gene expression analyses. Microarray analysis of gene expression is performed. Results of the microarray data identify the genes involved in the tolerance factor for cold. Genes involved in cold-tolerance adaptation will typically show at least a four-fold change in expression compared to the control cells exposed to the normal growing temperature.

Additional evaluations of the cell suspensions may also be conducted including, but not limited to, cell growth rates, cell densities, subculture frequency, and size and condition of cells.

The above-described techniques are also applicable to adapting animals to hostile environments. In certain embodiments, the animal is a mammal. As used herein, the term "mammal" refers to any mammal. Nonexclusive examples of such mammals include, but are not limited to, animals such as dogs, cats, horses, cattle, sheep, and goats. In other embodiments, the animal may be a bird. In yet other embodiments, the animal may be an aquatic species.

In one embodiment, the invention provides a method of adapting an animal to grow in a hostile environment, wherein an element of the hostile environment is selected from the group consisting of heat, cold, barometric pressure, excessive radiation, high carbon dioxide levels, low humidity, high humidity, chemical pollutants, disease, extreme salinity, reduced or increased exposure to sunlight, low water and drought conditions, excess water conditions or combinations thereof, including high and low levels or concentrations of any of the described conditions.

In some embodiments, the undifferentiated cells from animals suitable for use in the methods of the invention can be embryonic stem cells. Methods for isolating embryonic stem cells are well known to those of skill in the art, including, but not limited to, somatic nuclear transfer, cell fusion, and genetic manipulation techniques that create totipotent cells that are capable of generating all the tissues of the entire animal.

Alternatively, the undifferentiated animal cells can be obtained by methods comprising forming a diploid cell by uniting two haploid cells and proliferating the diploid cell in a weightless condition, wherein the diploid cell replicates itself but does not differentiate into specialized cells and tissues. More specifically, the egg and sperm are united using standard (IVF) techniques as described herein.

Culture conditions and media for culturing the undifferentiated cells according to the methods of the invention are well known to the skilled artisan as described above.

Various methods for culturing stem cells, e.g., embryonic stem cells (ESCs), may be used with the present invention. Typically, ESCs are grown in adherent culture systems such as on tissue culture plates. In certain aspects, culture plates for use in the invention may comprise a gel matrix such as a collagen or hydrogel matrix (e.g., a MATRIGEL™). In various embodiments, culture plates may be coated with, e.g., collagen IV, fibronectin, laminin, and vitronectin in combination may be used to provide a solid support for embryonic cell culturing and maintenance, as described in Ludwig et al. (2006). Matrix components which may be used with the present invention to coat tissue culture plates includes a collagen such as collagen IV, laminin, vitronectin, Matrigel™, gelatin, polylysine, thrombospondin (e.g., TSP-1, -2, -3, -4 and/or -5), and/or ProNectin-F™. Three dimensional support matrices for use in tissue culture have been previously described for example in U.S. Publication Nos. 20060198827 and 20060210596, each incorporated herein by reference. The skilled artisan will recognize that in certain aspects adherent tissue culture cells may be defined by the cell density or confluency. Thus, in some cases, methods of the invention involve expansion of proliferating cells from a high density to a lower density to facilitate further cell proliferation. For example, methods for expanding cells according to the invention may involve a first population of embryonic stem (ES) cells that is between about 50% and 99% confluent. For example, in certain aspects the first population of ES cells may be about or less than about 60%, 70%, 80%, 90% or 95% confluent. Furthermore, in certain aspects expansion or passage of adherent ES cells may involve seeding separated cells in fresh growth media. As used herein the term "seeding" cells means dispersing cells in growth media such that the resultant cell culture(s) are of approximately uniform density. Thus, seeding of cells may involve mixing separated cells with fresh growth media and/or spatially dispersing separated cells over the surface of a tissue culture plate.

Undifferentiated propagation of adherent colonies of ESCs may be accomplished with a Knockout (KO) serum-free culture system without the use of feeders by plating and growing the colonies on extracellular matrices (ECM) within a feeder-conditioned KO-DMEM medium supplemented with KOSR and fibroblast growth factor 2 (FGF2). Media available from commercial sources, such as Gibco Invitrogen Corporation, Grand Island, N.Y. Furthermore, it has been suggested that feeder conditioning may be replaced by substituting the medium with high concentrations of FGF2 and noggin. Alternatively, feeder conditioning was replaced by transforming growth factor-1 and human leukemia inhibitory factor (LIF) (in addition to FGF2) and growing the cells on human fibronectin, or by serum-free media supplemented with soluble factors including FGF2, activin A, transforming growth factor-β1 (TGF-β1), pipecolic acid, GABA, LiCL and culturing the cells on ECM components. In general, a key limitation of ESC culture systems is that they do not allow the propagation of pure populations of undifferentiated stem cells and their use typically involves some level of background differentiation. The stem cells most commonly follow a default pathway of differentiation into an epithelial cell type that grows either as a monolayer of flat squamous cells or form cystic structures. Most probably, this form of differentiation represents differentiation of human ESC (hESC) into extraembryonic endoderm.

In these adherent culture systems of colonies, the ESCs are most commonly propagated (mechanically and/or by using enzymatic digestion) as clusters, on a small scale. These culture systems are labor-intensive, highly variable, may contain undefined factors, and do not provide steady-state operating conditions. Most importantly, they do not typically allow for large scale production of standardized homogenous undifferentiated ESCs needed for the aforementioned uses.

Suspension culture bioreactors offer several advantages over the conventional use of static monolayer cultures. These systems facilitate the large-scale expansion of the cells in a homogeneous culture environment, thus decreasing the risk of culture variability. They are also less labor-intensive to operate and offer the possibility of computer control and monitoring of the culture conditions. Although bioreactors have been used to expand neural stem cells, mouse ES cells and differentiating hESCs within embryoid bodies (EBs), only recently some progress has been made towards the development of protocols for the feeder-free expansion of undifferentiated hESCs in suspension systems (see US20070212777, or *J. Biotechnology*, Vol. 132 (2), 227-236 (2007), which are herein incorporated by reference in its entirety).

Figure 3B:
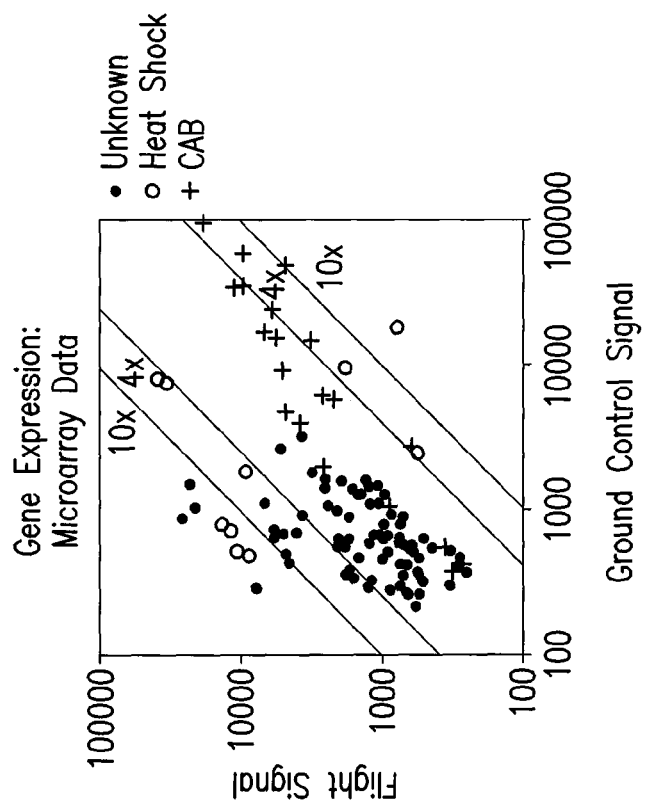
Figure 3A:
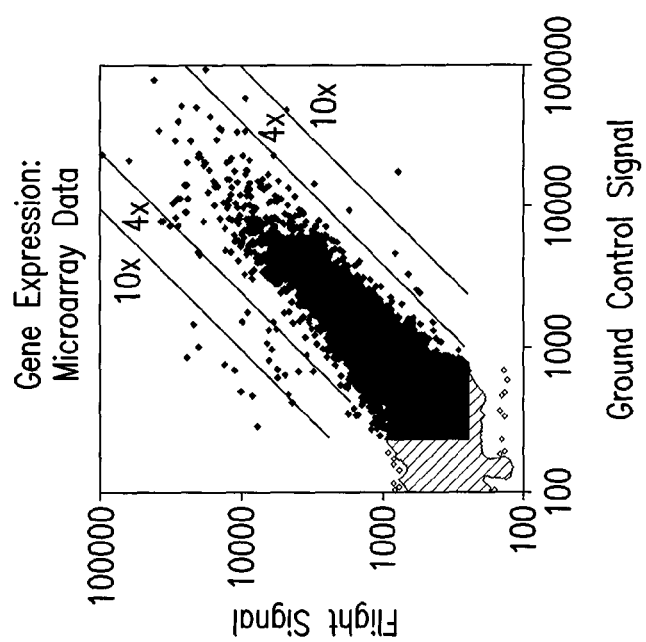

The present invention also provides methods of identifying genes associated with adaptation of a plant or animal to a hostile environment. Previous experiments demonstrated that seedlings from *Arabidopsis thaliana* grown under microgravity (weightless condition) exhibited a change in expression of select genes compared to their counterpart controls grown on Earth. The microarray data (FIG. 3) from these experiments showed that 182 genes were differentially expressed with at least a four-fold change in expression. Some of the differentially expressed genes were identified as heat-shock and/or CAB (light) genes. Using the same principles on which these experiments are based, the present invention provides methods for identifying specific genes differentially expressed between a control condition and a particular environmental condition. These identified genes may play a role in the adaptation of the plant or animal to that particular environment.

In one embodiment of the invention, the method comprises culturing undifferentiated cells from a plant or animal in a weightless condition that mimics at least one element of the hostile environment to which the plant or animal is to be adapted; selecting the cells that proliferate in said condition; and examining the gene expression profile of the selected cells in comparison to the gene expression profile of control cells; and identifying genes that have a change in expression level, wherein the identified genes are associated with adaptation to the hostile environment.

The change in expression level is at least 2-fold, at least 4-fold, at least 6-fold, at least 10-fold, at least 15-fold, or at least 20-fold. The change in expression level could be an increase in expression or a decrease in expression. Thus, particular environmental stimuli may produce both up-regulation and down-regulation of specific genes.

In one embodiment, the selected genes that are differentially expressed in the various environmental conditions can be further used to produce transgenic plants and animals with the desired adaptive characteristics by introducing these genes into cells that mature into plants or animals.

Therefore, the present invention further encompasses a plant or animal or undifferentiated cell thereof produced by the methods described herein, wherein said plant, animal or undifferentiated cell thereof comprises at least one identified gene that has a change in expression level as compared to the gene expression profile of control cell, wherein the identified genes are associated with adaptation to the hostile environment.

In one embodiment, a transgenic plant tolerant to environmental stresses, such as low temperature, freezing, and dehydration stresses, can be produced by introducing DNA encoding the protein of the interest into a host plant using genetic engineering techniques. Methods for introducing the gene into a host plant include indirect introduction such as the *Agrobacterium* infection method and direct introduction such as the particle gun method, polyethylene glycol method, liposome method, and microinjection method.

In the present invention, while the host for the transformant is not particularly limited, it is preferably a plant. The plant may be any cultured plant cells, the entire plant body of a cultured plant, plant organs (such as leaves, petals, stems, roots, rhizomes, or seeds), or plant tissues (such as epidermis, phloem, parenchyma, xylem, or vascular bundle). Plants may be monocotyledonous plants such as rice, maize, and wheat. When a cultured plant cell, plant body, plant organ or plant tissue is used as the host, the *Agrobacterium* infection method, particle gun method, or polyethylene glycol method can be employed to introduce the DNA encoding the protein of the present invention to transform this host plant by introducing a vector into plant sections. Alternatively, a vector can be introduced into a protoplast by electroporation to produce a transformed plant.

For example, when a gene is introduced into *Arabidopsis thaliana* by the *Agrobacterium* infection method, the step of infecting the plant with an *Agrobacterium* containing a plasmid comprising the gene of interest is essential. This step can be performed by the vacuum infiltration method [*CR Acad. Sci. Paris, Life Science,* 316:1194 (1993)]. Specifically, *Arabidopsis thaliana* is grown in a soil composed of equivalent portions of vermiculite and perlite. The *Arabidopsis thaliana* is immersed directly in a culture fluid of an *Agrobacterium*, containing a plasmid comprising the gene of interest, placed in a desiccator, and then sucked with a vacuum pump to 65-70 mmHg. Then, the plant is allowed to stand at room temperature for 5-10 min. The plant pot is transferred to a tray, which is covered with a wrap to maintain humidity. On the next day, the wrap is removed. The plant is grown in that state to harvest seeds.

Subsequently, the seeds are sown on MS agar medium supplemented with appropriate antibiotics to select those individuals which have the gene of interest. *Arabidopsis thaliana* grown on this medium are transferred to pots and grown there. As a result, seeds of a transgenic plant into which the gene of the interest has been introduced can be obtained. Generally, the genes are introduced into the genome of the host plant in a similar manner. However, due to differences in the specific locations on the genome into which the genes have been introduced, the expression of the introduced genes varies. This phenomenon is called "position effect." By assaying transformants with DNA fragments from the introduced gene as a probe by Northern blotting, it is possible to select those transformants in which the introduced gene is expressed more highly.

The confirmation that the gene of interest is integrated in the transgenic plant into which the gene of the present invention has been introduced and in the subsequent generation thereof can be made by extracting DNA from cells and tissues of those plants and detecting the introduced gene by PCR or Southern analysis, which are conventional methods in the art.

The expression level and expression site of a gene in a transgenic plant into which the gene of the present invention has been introduced can be analyzed by extracting RNA from cells and tissues of the plant and detecting the mRNA of the introduced gene by RT-PCR or Northern analysis, which are conventional methods in the art. Alternatively, the expression level and expression site can be analyzed directly by Western blotting or the like of the gene product of the present invention using an antibody against the above product.

In one embodiment, the gene of interest encodes a transcription factor. Because stress responses such as drought tolerance involve coordinated changes in many genes, the ability to affect many changes with one gene is an attractive proposition. Transcription factors can activate cascades of genes that function together to enhance stress tolerance. Transcription factors refer to a class of genes that control the degree to which other genes in a cell are activated. Transcription factors are able to recognize and bind to regions of DNA that have a specific sequence in the promoters of the genes they regulate. Thus, if a dozen genes all have that region of DNA somewhere in their promoters, they will all be regulated by the same transcription factor. Because transcription factors are key controlling elements of biological pathways, altering the expression levels of one or more transcription factors can control a variety of genes involved in the stress response.

In another embodiment, the gene of interest encodes a stress-induced protein. In an exemplary embodiment, the gene of interest encodes a heat-shock protein.

The control cells of the present invention to which the experimental cells are compared would include undifferentiated cells proliferating in a weightless condition exposed to the normal or native environmental element of that which is being varied in the experimental condition. For example, in a method to adapt a plant to grow in arid conditions, the undifferentiated cells from the plant would be exposed to a low humidity environment in the experimental condition and an environment having normal humidity for that particular plant species in the control condition.

In another embodiment, the method can be used for the production of vaccines to be used in animals and humans. Strains of *Salmonella* on orbit have previously been shown to demonstrate increases in virulence. See Wilson et al., *PLoS One* 12(3): e3923: 1-10.

In one embodiment, the invention provides a method of adapting a pathogenic microorganism to grow in a hostile, non-native environment comprising culturing the microorganism in a weightless condition that mimics at least one element of the hostile environment to which the microorganism is to be adapted; selecting the microorganisms that replicate in said condition; cultivating said selected microorganism to produce a modified strain of microorganism, wherein the microorganism is are adapted to grow in said hostile environment; and optionally evaluating the microorganism to determine the properties of said modified microorganism.

In another embodiment, the virulence of the modified microorganism is different than the virulence of the original non-adapted microorganism.

The technology described in this invention can be used to "force" the expression of genes on orbit to produced microorganisms, such as a bacteria or virus, with desired properties for vaccine production. By stressing, for example, a pathogenic microorganisms on orbit, modified strains of microorganisms can be produced. These modified microorganisms can include less virulent and/or more virulent strains of bacteria and viruses, which can then be utilized for the production of improved vaccines. The vaccines produced by this method can be applied to treatment and/or prevention of many animal and human diseases, including, but not limited to, hoof and mouth disease and brucellosis.

The foregoing detailed description has been given for clearness of understanding only and no unnecessary limitations should be understood therefrom as modifications will be obvious to those skilled in the art.

It is understood that the present invention is not limited to the particular methods and components, etc, described herein, as these may vary. It is also to be understood that the terminology used herein is used for the purpose of describing particular embodiments only, and is not intended to limit the scope of the present invention. It must be noted that as used herein, the singular forms "a," "an," and "the" include the plural reference unless the context clearly dictates otherwise.

All publications, patents, and patent applications identified above are incorporated herein by reference in their entirety. Although this invention has been described in relation to certain specific embodiments thereof, and many details have been set forth for purposes of illustration, it will be apparent to those skilled in the art that the invention is susceptible to additional embodiments and that certain of the details described herein may be varied considerably without departing from the basic principles of the invention.

I claim:

1. A method of adapting a citrus plant to grow in a cold environment, the method comprising:

providing replicating citrus parenchyma cells to produce a cell suspension culture comprising a plurality of undifferentiated citrus parenchyma cells;

culturing the cell suspension culture comprising the plurality of undifferentiated citrus parenchyma cells while simultaneously exposing the cell culture to both a microgravity condition and a cold environment to which the citrus plant is to be adapted;

harvesting citrus cells that replicate during the step of culturing, wherein the culturing simultaneously exposes the cell suspension culture to both the microgravity condition and the cold environment, to cause the plurality of undifferentiated citrus parenchyma cells to express genes that enable the harvested cells to adapt to the cold environment; and sequentially removing the harvested citrus cells from the microgravity condition, and cultivating the harvested cells to produce a mature citrus plant;

wherein the cold environment is a temperature of about 25° F. or less.

2. The method of claim 1 further comprising evaluating said mature plant.

3. The method of claim 2, wherein said mature plant is evaluated for at least one of length of survival, growth rate, reproductive capability, cell structure, gene expression, or combinations thereof.

4. The method of claim 1, wherein the parenchyma cells are obtained from uniting a pollen and ovule of a citrus plant prior to exposure to the microgravity condition.

5. The method of claim 1, wherein the parenchyma cells are obtained by uniting a pollen and an ovule of a citrus plant in the microgravity condition, wherein said parenchyma cells obtained from said union do not develop into differentiated cells.

6. The method of claim 1, further comprising steps of:
    examining a gene expression profile of the harvested citrus cells in comparison to the gene expression profile of control citrus cells; and
    identifying genes that have a change in expression level as compared to the gene expression profile of the control cells; wherein said identified genes are associated with adaptation to the cold environment.

7. The method of claim 6, wherein the change in expression level is at least four fold in comparison to the expression profile of the control cells.

8. The method of claim 1, further comprising a step of excising the parenchyma cells from a cellular sample, the step of excising occurring prior to the step of replicating.

* * * * *